(12) United States Patent
McNaughton et al.

(10) Patent No.: US 11,890,555 B2
(45) Date of Patent: Feb. 6, 2024

(54) METHOD AND SYSTEM FOR BUOYANT SEPARATION

(71) Applicant: Akadeum Life Sciences, Inc., Ann Arbor, MI (US)

(72) Inventors: Brandon H. McNaughton, Ann Arbor, MI (US); John G. Younger, Ann Arbor, MI (US); Leo Ostruszka, Ann Arbor, MI (US); Jonathan Roussey, Ann Arbor, MI (US); Gene Parunak, Ann Arbor, MI (US); Aaron Kehrer, Ann Arbor, MI (US)

(73) Assignee: Akadeum Life Sciences, Inc., Ann Arbor, MI (US)

( * ) Notice: Subject to any disclaimer, the term of this patent is extended or adjusted under 35 U.S.C. 154(b) by 0 days.

(21) Appl. No.: 18/105,429

(22) Filed: Feb. 3, 2023

(65) Prior Publication Data
US 2023/0182043 A1   Jun. 15, 2023

Related U.S. Application Data

(63) Continuation of application No. 17/671,271, filed on Feb. 14, 2022, which is a continuation of application
(Continued)

(51) Int. Cl.
*B01D 21/00* (2006.01)
*B01L 3/00* (2006.01)
(Continued)

(52) U.S. Cl.
CPC ..... *B01D 21/0084* (2013.01); *B01D 21/2433* (2013.01); *B01D 21/262* (2013.01);
(Continued)

(58) Field of Classification Search
CPC ............ B01D 21/0084; B01D 21/2433; B01D 21/262; B01L 3/5021; B01L 2200/026;
(Continued)

(56) References Cited

U.S. PATENT DOCUMENTS

| 3,381,283 A | 4/1968 | Gyorgy et al. |
| 3,586,064 A | 6/1971 | Brown et al. |

(Continued)

FOREIGN PATENT DOCUMENTS

| DE | 3381283 | 4/1990 |
| EP | 0778944 B1 | 11/1999 |

(Continued)

OTHER PUBLICATIONS

Corrosionpedia—Diaphragm Pump—Published: Oct. 2, 2014 Updated: May 4, 2019 (Year: 2019).

(Continued)

*Primary Examiner* — Walter D. Griffin
*Assistant Examiner* — Shuyi S. Liu
(74) *Attorney, Agent, or Firm* — Jeffrey Schox; Caitlin Ploch

(57) ABSTRACT

A method and system for buoyant separation of a target constituent of a sample, the method comprising: at a process chamber, combining a volume of substrates having a first density with the sample, thereby producing a population of target-bound complexes comprising the target constituent bound to at least a portion of the volume of substrates; within the process chamber, physically separating the population of target-bound complexes from the sample based upon interaction between the volume of substrates and an applied force; aggregating the population of target-bound complexes at a collection region of the process chamber; extracting the population of target-bound complexes from the process chamber; and processing the target constituent (Continued)

from the population of target-bound complexes for further analysis.

17 Claims, 27 Drawing Sheets

Related U.S. Application Data

No. 16/004,874, filed on Jun. 11, 2018, now Pat. No. 11,291,931, which is a continuation-in-part of application No. 14/969,446, filed on Dec. 15, 2015, now Pat. No. 10,195,547.

(60) Provisional application No. 62/092,019, filed on Dec. 15, 2014, provisional application No. 62/189,518, filed on Jul. 7, 2015, provisional application No. 62/616,647, filed on Jan. 12, 2018, provisional application No. 62/517,543, filed on Jun. 9, 2017.

(51) Int. Cl.
  *B01D 21/26* (2006.01)
  *B01D 21/24* (2006.01)
  *G01N 33/49* (2006.01)

(52) U.S. Cl.
  CPC ....... *B01L 3/5021* (2013.01); *B01L 2200/026* (2013.01); *B01L 2200/0652* (2013.01); *B01L 2400/06* (2013.01); *G01N 33/491* (2013.01)

(58) Field of Classification Search
  CPC ......... B01L 2200/0652; B01L 2400/06; G01N 33/491
  See application file for complete search history.

(56) References Cited

U.S. PATENT DOCUMENTS

| | | | |
|---|---|---|---|
| 3,692,493 A * | 9/1972 | Terasaki | G01N 33/491 604/416 |
| 3,920,549 A | 11/1975 | Gigliello et al. | |
| 4,086,060 A | 4/1978 | Hermann | |
| 4,464,254 A | 8/1984 | Dojki et al. | |
| 4,487,700 A | 12/1984 | Kanter | |
| 4,689,151 A | 8/1987 | Kosikowski et al. | |
| 4,714,680 A | 12/1987 | Civin | |
| 4,845,025 A | 7/1989 | Lary et al. | |
| 5,116,724 A | 5/1992 | Delaage et al. | |
| 5,182,192 A * | 1/1993 | Steplewski | C07K 16/30 424/9.34 |
| 5,246,829 A | 9/1993 | Delaage et al. | |
| 5,266,199 A | 11/1993 | Tsukagoshi et al. | |
| 5,339,830 A | 8/1994 | Blake | |
| 5,354,483 A | 10/1994 | Furse | |
| 5,594,164 A | 1/1997 | Bull | |
| 5,639,382 A | 6/1997 | Brown | |
| 5,730,864 A | 3/1998 | Delsalle et al. | |
| 5,853,600 A | 12/1998 | McNeal et al. | |
| 5,874,266 A | 2/1999 | Palsson | |
| 6,036,940 A | 3/2000 | Ju et al. | |
| 6,151,113 A | 11/2000 | Odonohue et al. | |
| 6,221,315 B1 | 4/2001 | Giesler et al. | |
| 6,261,537 B1 | 7/2001 | Klaveness et al. | |
| 6,264,917 B1 | 7/2001 | Klaveness et al. | |
| 6,331,289 B1 | 12/2001 | Klaveness et al. | |
| 6,416,739 B1 | 7/2002 | Rogerson et al. | |
| 6,506,167 B1 | 1/2003 | Ishimoto et al. | |
| 6,528,039 B2 | 3/2003 | Unger | |
| 6,544,424 B1 | 4/2003 | Shevitz | |
| 6,569,340 B2 | 5/2003 | Kopf | |
| 6,652,136 B2 | 11/2003 | Marziali | |
| 6,723,303 B1 | 4/2004 | Quay | |
| 6,919,031 B2 | 7/2005 | Blumenschein et al. | |
| 7,524,641 B2 | 4/2009 | Jurgensen et al. | |
| 7,704,393 B2 | 4/2010 | Noh et al. | |
| 7,915,540 B2 | 3/2011 | Oggioni | |
| 8,048,320 B2 | 11/2011 | Leach et al. | |
| 8,066,127 B2 | 11/2011 | Coelho et al. | |
| 8,177,072 B2 | 5/2012 | Chapman et al. | |
| 8,183,039 B2 | 5/2012 | Schmitz et al. | |
| 8,290,714 B2 | 10/2012 | Ignatius et al. | |
| 8,513,032 B2 | 8/2013 | Jablonski et al. | |
| 8,540,082 B2 | 9/2013 | Kelland et al. | |
| 8,617,884 B2 | 12/2013 | Berenson et al. | |
| 8,747,289 B2 | 6/2014 | Coelho | |
| 8,834,698 B2 | 9/2014 | Lau et al. | |
| 8,835,186 B2 * | 9/2014 | Jablonski | G01N 33/54313 436/523 |
| 9,011,819 B2 | 4/2015 | Rychak | |
| 9,039,999 B2 | 5/2015 | Campton et al. | |
| 9,120,095 B2 | 9/2015 | Oconnell | |
| 9,234,890 B2 | 1/2016 | Adams et al. | |
| 9,506,930 B2 | 11/2016 | Ignatius et al. | |
| 9,528,088 B2 | 12/2016 | Berenson et al. | |
| 9,599,545 B2 | 3/2017 | Coelho | |
| 9,695,394 B1 | 7/2017 | Coelho et al. | |
| 9,766,237 B2 | 9/2017 | Jablonski et al. | |
| 9,797,817 B2 | 10/2017 | McNaughton et al. | |
| 9,821,111 B2 | 11/2017 | Coelho et al. | |
| 9,857,361 B2 | 1/2018 | Wanders et al. | |
| 10,195,280 B2 | 2/2019 | De Mollerat Du Jeu et al. | |
| 10,273,504 B2 | 4/2019 | Miltenyi et al. | |
| 10,302,536 B2 | 5/2019 | Shi et al. | |
| 10,407,486 B2 | 9/2019 | Schmitz et al. | |
| 10,479,976 B2 | 11/2019 | Shi et al. | |
| 10,585,088 B2 | 3/2020 | Gohel et al. | |
| 10,684,172 B2 | 6/2020 | Carron et al. | |
| 10,792,362 B2 | 10/2020 | De Mollerat Du Jeu et al. | |
| 10,794,900 B2 | 10/2020 | Wanders et al. | |
| 10,859,477 B2 | 12/2020 | Nakamura et al. | |
| 10,934,519 B2 | 3/2021 | Roy et al. | |
| 11,007,285 B2 | 5/2021 | Butts et al. | |
| 11,339,407 B2 | 5/2022 | Waters et al. | |
| 2002/0048819 A1 | 4/2002 | Alley | |
| 2003/0066850 A1 | 4/2003 | Young | |
| 2003/0104359 A1 | 6/2003 | Cuthbertson et al. | |
| 2004/0023222 A1 | 2/2004 | Russell et al. | |
| 2004/0166029 A1 | 8/2004 | Losada et al. | |
| 2005/0059163 A1 | 3/2005 | Dastane et al. | |
| 2006/0054191 A1 | 3/2006 | Higuchi et al. | |
| 2006/0131236 A1 | 6/2006 | Belfort et al. | |
| 2007/0015191 A1 | 1/2007 | Bitner et al. | |
| 2007/0036722 A1 | 2/2007 | Rongved et al. | |
| 2007/0075016 A1 | 4/2007 | Leach | |
| 2007/0190584 A1 | 8/2007 | Jurgensen et al. | |
| 2008/0034509 A1 | 2/2008 | Nuennerich et al. | |
| 2009/0042284 A1 | 2/2009 | Tachibana et al. | |
| 2010/0285606 A1 | 11/2010 | Phillips et al. | |
| 2011/0097816 A1 | 4/2011 | Goodwin | |
| 2011/0236884 A1 | 9/2011 | Jablonski et al. | |
| 2012/0202225 A1 | 8/2012 | Knutson et al. | |
| 2013/0029411 A1 | 1/2013 | Roy et al. | |
| 2013/0280767 A1 | 10/2013 | Kobayashi et al. | |
| 2014/0161688 A1 | 6/2014 | Campton et al. | |
| 2014/0277672 A1 | 9/2014 | Manzarek et al. | |
| 2015/0011013 A1 | 1/2015 | Campton et al. | |
| 2015/0021963 A1 | 1/2015 | Reed | |
| 2015/0219636 A1 | 8/2015 | Rychak et al. | |
| 2015/0260178 A1 | 9/2015 | Giessbach | |
| 2015/0320924 A1 | 11/2015 | Flieg et al. | |
| 2016/0167061 A1 | 6/2016 | McNaughton et al. | |
| 2017/0001191 A1 | 1/2017 | Biadillah et al. | |
| 2017/0014819 A1 | 1/2017 | U'Ren et al. | |
| 2017/0059552 A1 | 3/2017 | Campton et al. | |
| 2017/0183619 A1 | 6/2017 | Coelho et al. | |
| 2018/0171295 A1 | 6/2018 | Shi et al. | |
| 2018/0290077 A1 | 10/2018 | McNaughton et al. | |
| 2020/0072834 A1 | 3/2020 | Busa et al. | |

(56) References Cited

U.S. PATENT DOCUMENTS

2020/0276540 A1 9/2020 Smyslova et al.
2021/0180108 A1 6/2021 Kim et al.

FOREIGN PATENT DOCUMENTS

| EP | 1073716 B1 | 4/2004 |
|---|---|---|
| EP | 2104488 B1 | 10/2016 |
| GB | 1407267 A | 9/1975 |
| JP | 2001120964 A | 5/2001 |
| JP | 2014521333 A | 8/2014 |
| WO | 2011052927 A2 | 5/2011 |
| WO | 2012090863 A1 | 7/2012 |
| WO | 2013096157 A1 | 6/2013 |
| WO | 2015133972 A1 | 9/2015 |
| WO | 2017109072 A1 | 6/2017 |
| WO | 2017190117 A1 | 11/2017 |

OTHER PUBLICATIONS https://en.wikipedia.org/wiki/Diaphragm_pump (Year: 2021).
https://www.yamadapump.com/what-is-a-double-diaphragm-pump/#:-:text=A (Year: 2021).
Mud Sucker Diaphragm Pumps, https://wastecorp.com/ms-faqs (Year: 2021).
Moon, Sang Ho, "Bio-device for extracting hematopoietic stem cells and mesenchymal stem cells in peripheral blood", Translation of WO 2011/052927 A2, 2011, WIPO, p. 1-23 (Year: 2011).
Wang, Meiyao, "Quantifying CD4 receptor protein in two human CD4+ lymphocyte preparations for quantitative flow cytometry", Clinical proteomics, 11 (1), 43. https://doi.org/10.1186/1559-0275-11-43.

* cited by examiner

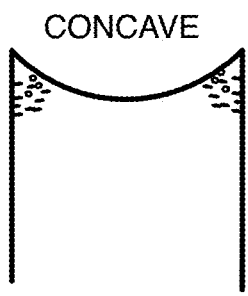 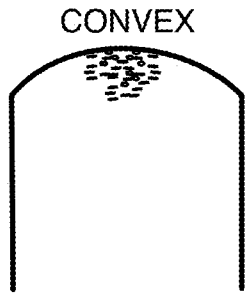 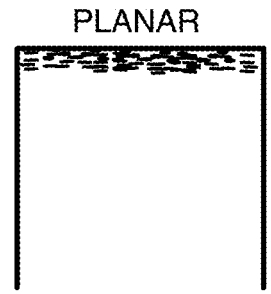
FIGURE 2A  FIGURE 2B  FIGURE 2C
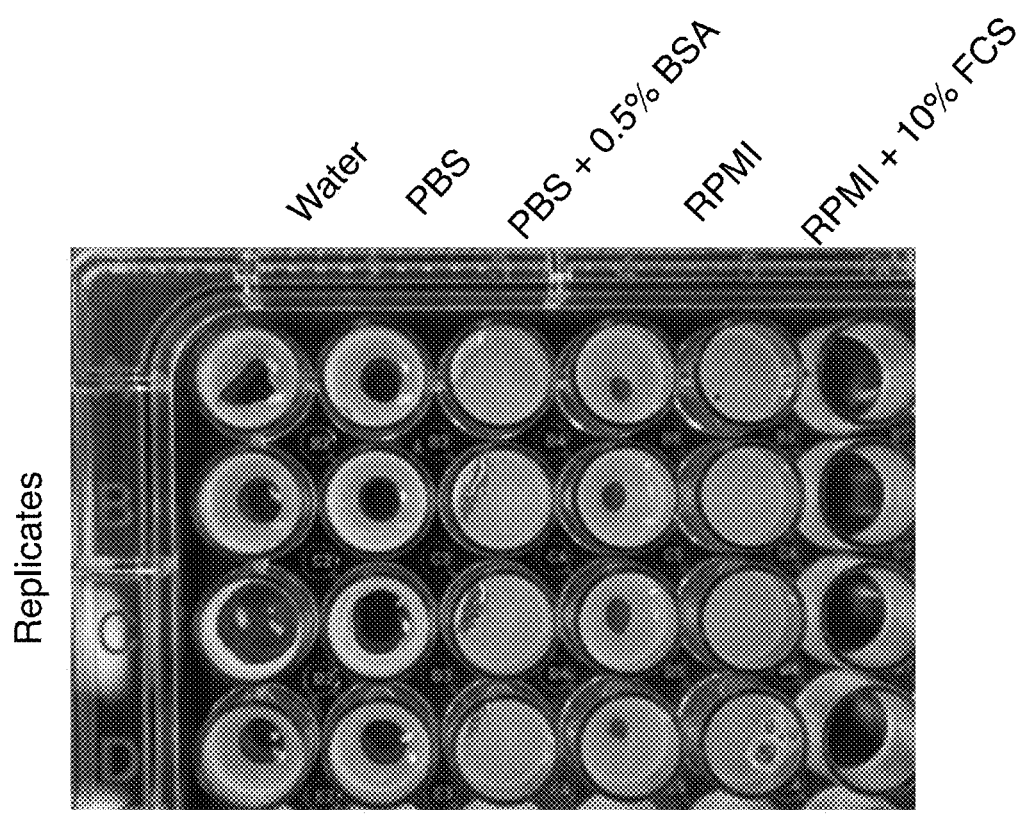
FIGURE 2D Linear
Frustoconical Curved
Frustoconical Prismatic Before Contact Ring After Contact Buoyant
Particles Void Sample
Fluid

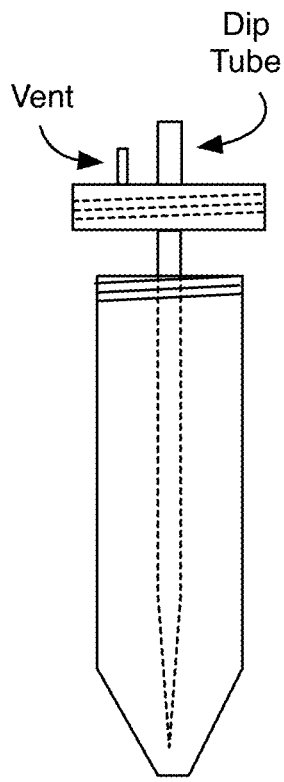
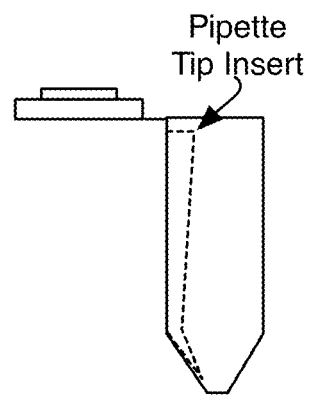
FIGURE 12B
FIGURE 12A
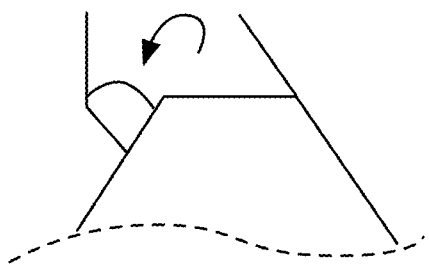
Particle-containing meniscus displaced into sample cup at apex of conical geometry
FIGURE 13

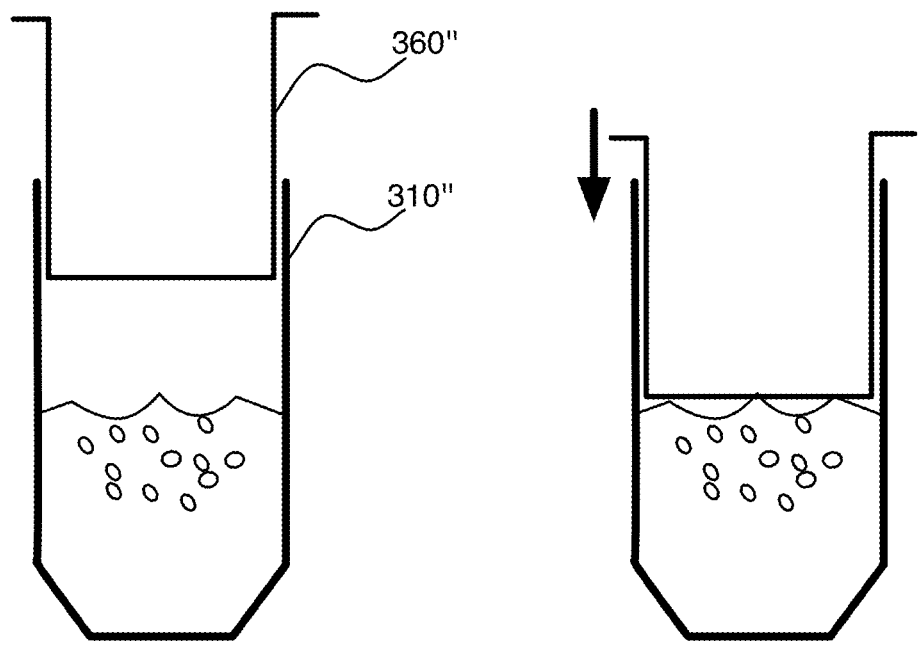
FIGURE 16C
FIGURE 16D
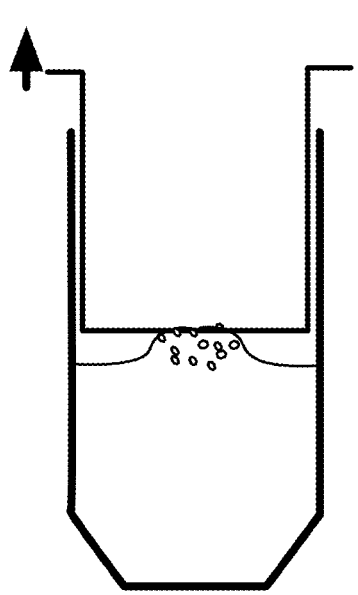
FIGURE 16E
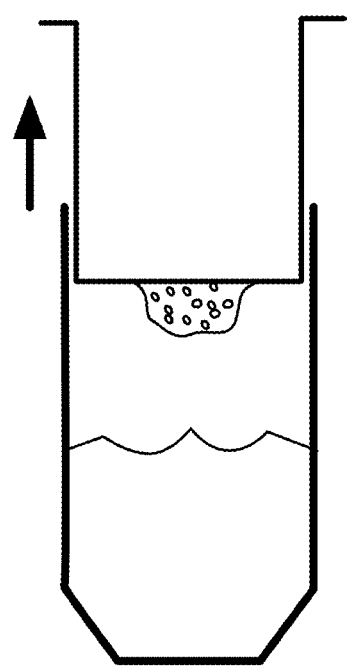
FIGURE 16F

Compression of the bag

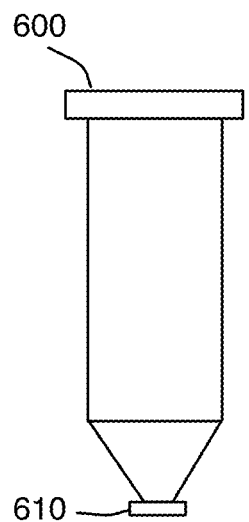
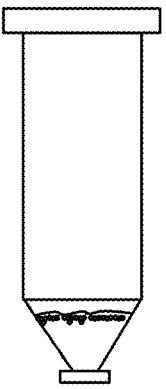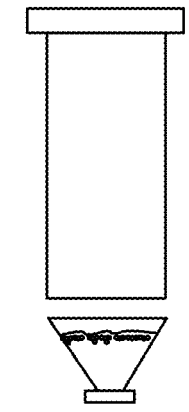
FIGURE 19A      FIGURE 19B
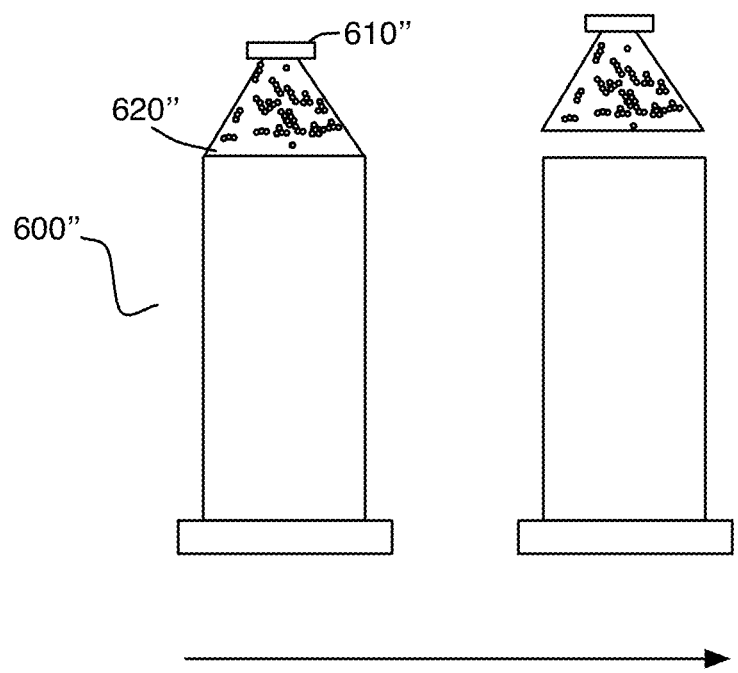
FIGURE 19C

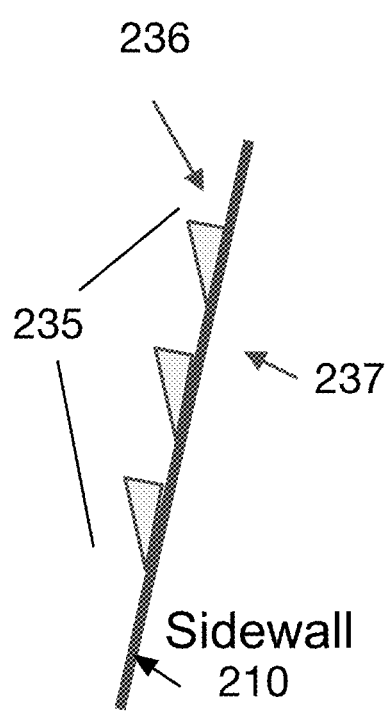
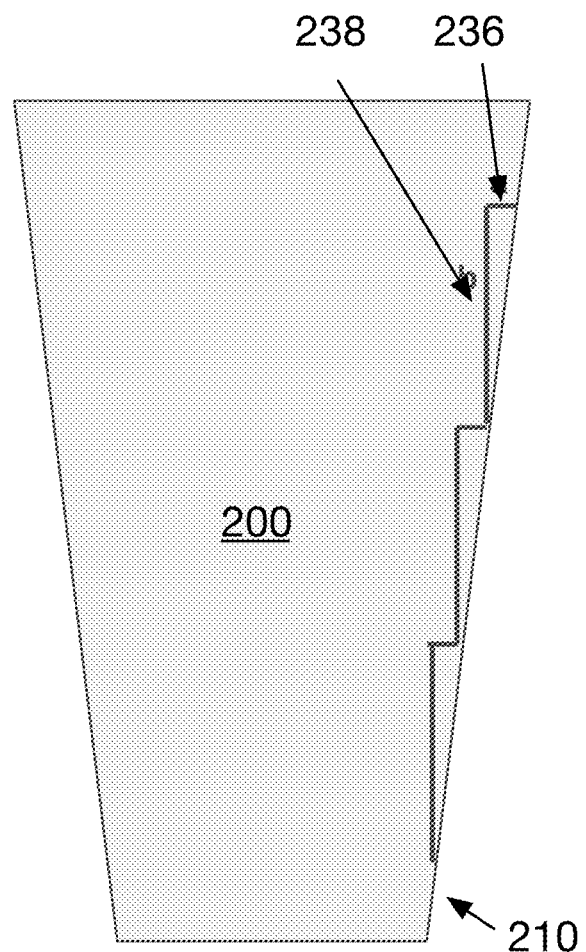
FIGURE 20A
FIGURE 20B

METHOD AND SYSTEM FOR BUOYANT SEPARATION

CROSS-REFERENCE TO RELATED APPLICATIONS

This application is a continuation of U.S. application Ser. No. 17/671,271, filed 14 Feb. 2022, which is a continuation of U.S. application Ser. No. 16/004,874, filed 11 Jun. 2018, which is a continuation-in-part of U.S. application Ser. No. 14/969,446, filed 15 Dec. 2015, which claims the benefit of U.S. Provisional Application Ser. No. 62/092,019, filed on 15 Dec. 2014 and U.S. Provisional Application Ser. No. 62/189,518 filed on 7 Jul. 2015, which are each incorporated herein in their entirety by this reference. U.S. application Ser. No. 16/004,874, filed 11 Jun. 2018 also claims the benefit of U.S. Provisional Application No. 62/616,647 filed on 12 Jan. 2018 and 62/517,543 filed on 9 Jun. 2017, which are both incorporated herein in their entirety by this reference.

TECHNICAL FIELD

This invention relates generally to separation methods and systems in the fields of biological sample processing. More specifically, it relates to an improved method and system for buoyant separation of particles in a sample of biological fluid.

BACKGROUND

In research and diagnostic applications, it is often important to be able to isolate one or more types of particles of a sample. Isolation of target components in an efficient and high throughput manner can thus have a significant impact in healthcare applications, biological research, research in the food industry, and medical research. Components for isolation and extraction can include cells, proteins, nucleic acids, lipids, and other particles commonly found in biological fluid, and in one example, efficient isolation of rare cancerous cells (e.g., circulating tumor cells) in a biological sample can be used to detect and/or diagnose cancer for a patient at an early stage where intervention is critical. There are several conventional setups used for particle isolation from samples, implementing techniques derived from one or more of: fluorescence activated sorting, magnetic sorting, filtration, electrophoretic separation, and other methods of separation. However, conventional particle isolation systems are typically inefficient, are not high-throughput, are labor intensive, are prone to user-error, and require large systems, necessitating a significant amount of training, and/or contributing to untrustworthy analyses. Conventional setups are also typically expensive to operate, from time, labor, and cost perspectives, which can provide limits upon the completeness of an analysis performed using such set-ups.

Thus, there is a need in the biological sample processing field to create an improved method and system for buoyant separation of target components of a sample. This invention provides such an improved method and system.

BRIEF DESCRIPTION OF THE FIGURES

FIGS. 2A-2C depict variations of interactions between sample fluid and a process chamber in an embodiment of a method for buoyant separation of a target constituent of a sample.

FIG. 2D depicts specific examples of variations of interactions between sample fluid and a process chamber in embodiments of a method for buoyant separation of a target constituent of a sample.

FIGS. 12A and 12B depict examples of process chambers used in a method for buoyant separation of a target constituent of a sample.

FIG. 13 depicts an example of a process chamber for buoyant separation of a target constituent of a sample.

FIGS. 16A-16F depict a variation of an embodiment of a system for buoyant separation of a target constituent of a sample.

FIGS. 19A-19C depict an alternative embodiment of a system for buoyant separation of a target constituent of a sample.

FIGS. 20A-20B depict variations of a subcomponent of a process chamber used in an embodiment of a system for buoyant separation of a target constituent of a sample.

DESCRIPTION OF THE PREFERRED EMBODIMENTS

The following description of preferred embodiments and examples of the invention is not intended to limit the invention to these preferred embodiments and examples, but rather to enable any person skilled in the art to make and use this invention.

1. Method

Figure 1A:
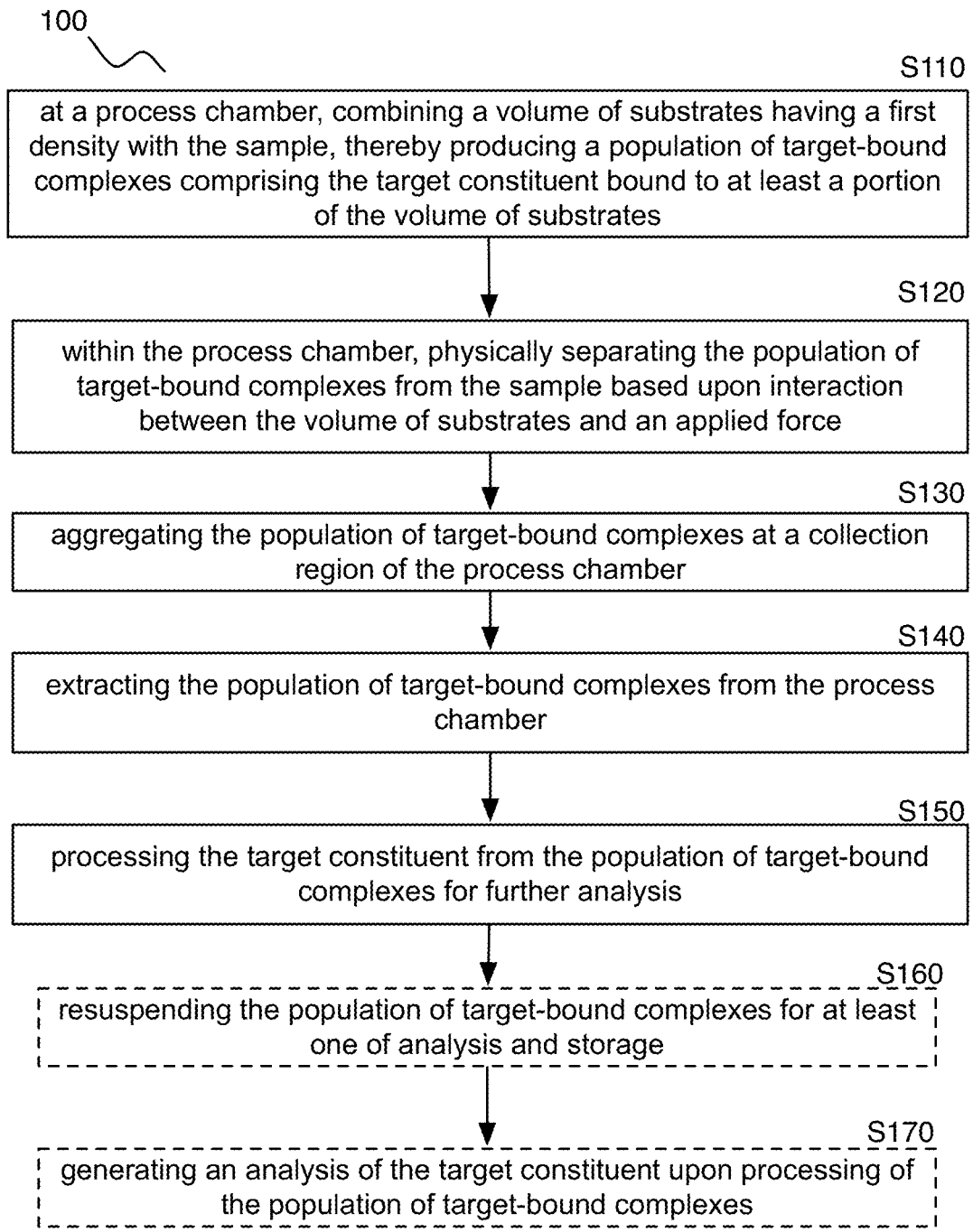
FIGS. 1A and 1B are flowchart schematics of embodiments of a method for buoyant separation of a target constituent of a sample.
Figure 1B:
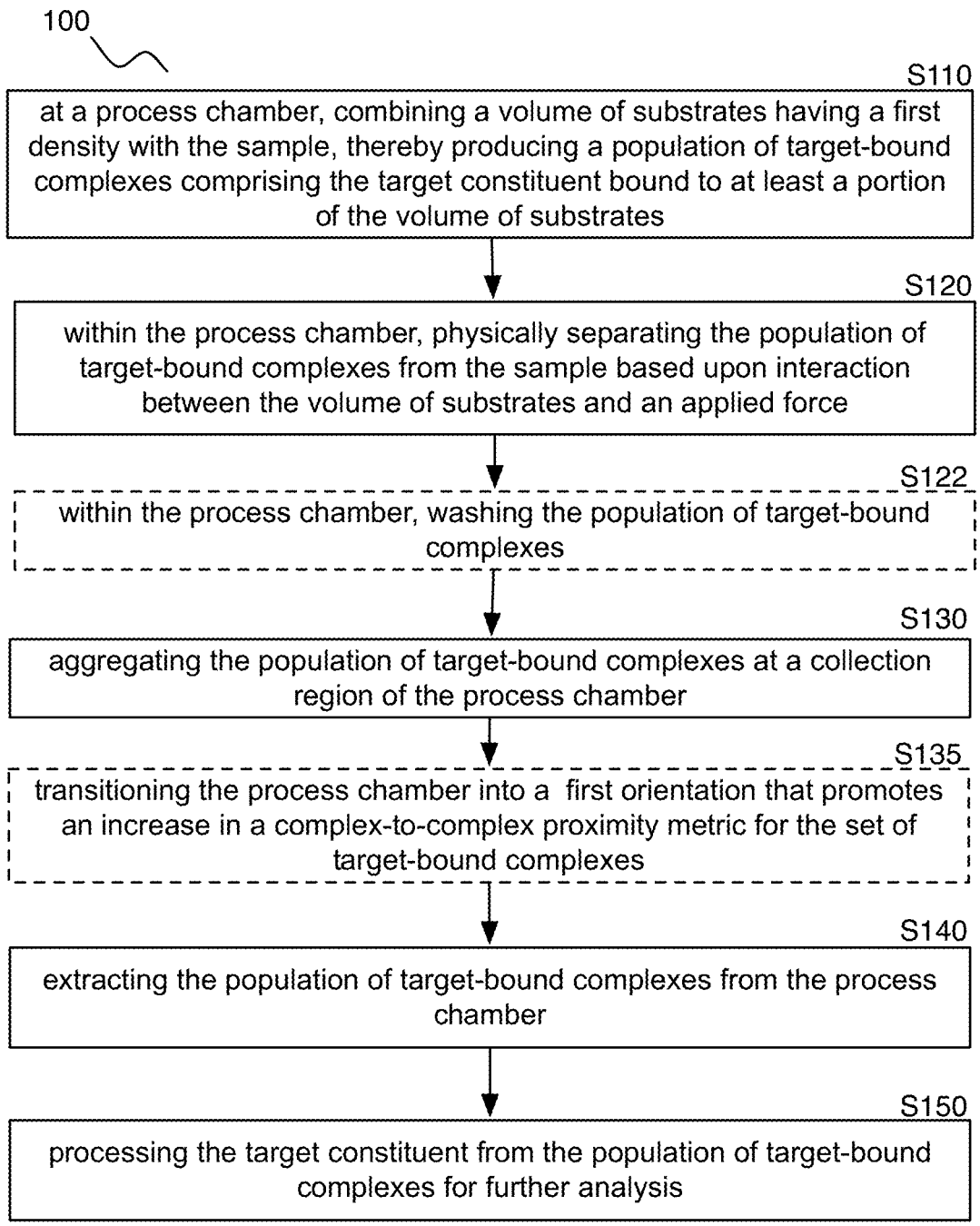

As shown in FIGS. 1A and 1B, an embodiment of a method 100 for buoyant separation of a target constituent of a sample comprises: at a process chamber, combining a volume of substrates having a first density with the sample, thereby producing a population of target-bound complexes comprising the target constituent bound to at least a portion of the volume of substrates S110; within the process chamber, physically separating the population of target-bound complexes from the sample based upon interaction between the volume of substrates and an applied force S120; aggregating the population of target-bound complexes at a collection region of the process chamber S130; extracting the population of target-bound complexes from the process chamber S140; and processing the target constituent from the population of target-bound complexes for further analysis S150. However, the method 100 can additionally or alternatively be implemented in any other suitable steps, such as in a manner analogous to U.S. application Ser. No. 14/969,446, filed 15 Dec. 2015, which is incorporated in its entirety by this reference.

The method 100 functions to provide a process for efficiently separating target constituents from a sample with a low amount of effort from research or clinical personnel. The method 100 also functions to facilitate downstream analyses (e.g., polymerase chain reaction-based assays, lateral flow assays, culture-based assays, etc.) of isolated and collected target constituents, for research applications, clinical applications, and/or food industry applications. Preferably, the method 100 can be applied to a large sample volume (e.g., 35 mL sample volumes, sample volumes over 5 mL, etc.), in order to extract one or more target components from the large sample volume. However, the method 100 can additionally or alternatively be applied to any other suitable sized sample volume (e.g., sample volumes smaller than or equal to 5 mL). The method 100 preferably utilizes passively applied forces (e.g., gravitational force) and/or actively applied forces (e.g., centrifugal force) to separate target constituents from a bulk sample based upon density differences between bound target constituents and the bulk sample; however, the method 100 can additionally or alternatively use any other physical parameter and associated separation mechanism to enhance isolation of a target constituent from a biological sample. For instance, in one variation, buoyant separation can be enhanced with magnetic manipulation of buoyant particles, by coupling a target constituent to particles having buoyant and magnetic-dual functionality. Upon separation of the target constituent from the sample, extraction of the target constituent can be performed according to the method 100. Additionally and/or alternatively, non-target constituents can be bound to buoyant substrates and removed according to the method 100. In other variations, a non-target constituent of the sample can be tagged with magnetic substrates and drawn or repelled to a desired region of a process chamber (e.g., wall of the process chamber), while the target constituent that has been tagged with buoyant substrates is separated from the sample volume. However, any other suitable mode of separation process can be implemented in addition to or in substitution of the separation methods described.

Furthermore, the method 100 can be used to simultaneously or sequentially separate each of a set of target constituents from a bulk sample, based upon selective coupling of each of the set of target constituents to an associated substrate volume that can be individually isolated based upon a feature (e.g., physical feature, chemical feature, etc.). In variations, the method 100 can be used for separation of target cell and/or target analyte constituents from a biological sample, by using buoyant particles that facilitate concentration of the target constituents to a collection location (e.g., an extremum most opposite a gravitational or centrifugal force). The method 100 is preferably implemented, at least in part, using elements of the system 200 described in Section 2 below; however, the method 100 can additionally or alternatively be implemented using any other suitable system.

In a specific example, the method 100 can be used to provide buoyancy-activated separation and/or extraction of target constituents of a sample from a bulk sample volume of 1 Liter within 30 minutes. In a second specific example, the method 100 can be used to provide buoyancy-activated separation and/or extraction of target constituents of a sample from a bulk sample volume of 50 mL within 15 minutes. However, variations of the method 100 can alternatively be tuned to enable separation according to any other suitable timeline.

1.1 Method—Tagging with Buoyant Substrates

Block S110 recites: at a process chamber, combining a volume of substrates having a first density with the sample, thereby producing a population of target-bound complexes comprising the target constituent bound to at least a portion of the volume of substrates. Block S110 functions to provide interaction between the target constituent and the volume of substrates, thereby enabling selective manipulation of the target constituent in subsequent blocks of the method 100. Block S110 is preferably implemented using an embodiment, variation, and/or example of the process chamber described in Section 2 below; however, Block S110 can additionally or alternatively be implemented using any other suitable process chamber(s) for combination of a sample with a volume of a process material. Furthermore, variations of Block S110 can include receiving a sample volume having a population of target-bound complexes, where combination and/or complexification was performed in a separate process chamber. Embodiments, variations, and/or examples of Block S110 are further described in U.S. application Ser. No. 14/969,446, filed 15 Dec. 2015.

In Block S110 substrates of the volume of substrates preferably comprise substrate particles (e.g., beads, spheres, micelles, microbubbles) and can include any one or more of: plastic beads (e.g., polypropylene beads, polyethylene beads, etc.), glass beads, lipid beads (e.g., stabilized liposome-based beads), hollow beads, solid beads, liquid-filled beads, and any other suitable type of particle. Furthermore, while substrates used in Block S110 are preferably substrate particles, Block S110 can additionally or alternatively include using planar or non-planar substrates (e.g., plates, surfaces, surface coatings, etc.), or substrates having any other suitable morphology that facilitates separation of the target constituent from the sample.

The substrates are preferably characterized by a first density lower than that of the density (i.e., a second density) of fluid of the sample (e.g., ranging from 0.1 g/cm$^3$ and 0.99 g/cm$^3$). As such, substrates of the volume of substrates are preferably configured to float within the sample to facilitate separation in subsequent blocks of the method 100 (e.g., buoyant particles). However, substrates of the volume of substrates can alternatively be configured with any other suitable density relative to that of the density of fluid and/or untargeted constituents of the sample to facilitate separation.

In examples, the substrates have a diameter from 10 nm to 100 nm in targeting analytes or 1 μm to 30 μm in targeting cells; however, the particles can have any other suitable dimension configured facilitate efficient binding with elements of the target constituent.

Figure 1C:
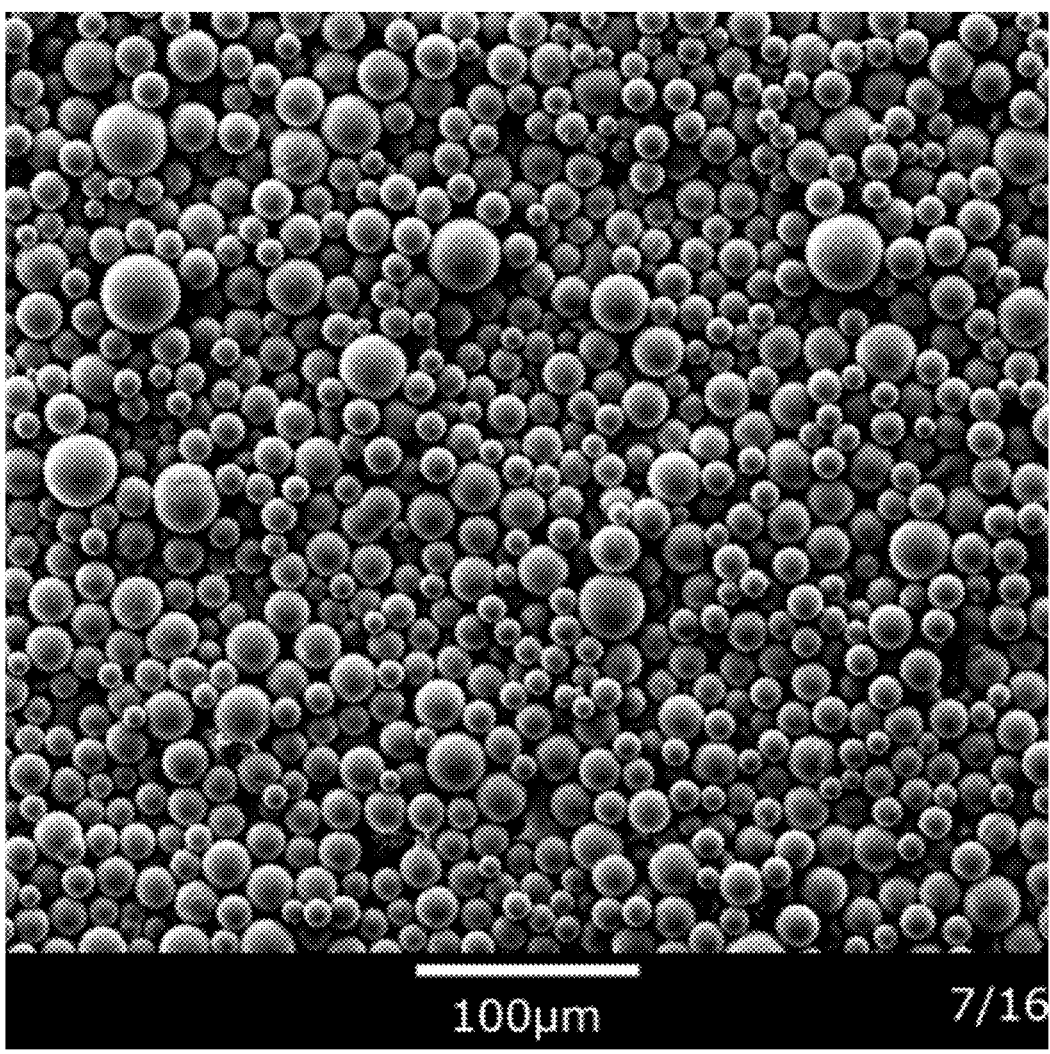
FIG. 1C depicts an optical micrograph of a variation of substrates used in an embodiment of a method for buoyant separation of a target constituent of a sample.

In one variation, the volume of substrates comprises silica beads having a density less than that of fluid of the sample, wherein the silica beads are treated with a moiety (e.g., Streptavidin for biotin binding, an antibody for formation of an antibody-antigen complex, another moiety, etc.) configured to selectively couple with associated portions of the target constituent (e.g., cell, analyte) of the sample. In a second variation, the volume of substrates comprises microbubbles (e.g., gas-filled microparticles, hollow microspheres, colloidal bubbles) that can be spheroidal, skirted, ellipsoidal or any other suitable three-dimensional shape. The shape of the microbubbles can vary dynamically in response to the fluid dynamics of the sample volume (e.g., changing from one shape to another dictated by gravity, viscosity, and surface tension), but can alternatively be a fixed shape. In a specific example, as shown in FIG. 1C, the microbubbles are comprised of borosilicate glass that can include a particle shell surrounding a particle core (e.g., gas filled, fluid-filled, particle-filled, etc.). However, the particle shell can be alternatively composed of any other suitable material including lipids, proteins, surfactants, polymers, and/or any suitable combination thereof. In this example, the glass microbubbles can be fabricated with a fixed spheroidal shape defining a particle diameter (e.g., ranging from between 5 to 30 micron), and a particle shell thickness (e.g., less than 2 micron thick). In solution, the volume of microbubbles to volume target constituent (e.g., target cell) ratio preferably ranges between 1:2 to 5:1. However, the substrates can be of any other suitable composition, shape, density, and/or dimension.

Furthermore, the substrates can be configured with moieties for binding to the target constituent (e.g., red blood cells, white blood cells, T-cells, circulating tumor cells, stem cells, etc.) and can additionally or alternatively include any one or more of: charge-based moieties, nucleic acid-targeting moieties, protein-based moieties (e.g., cell adhesion molecules, growth factors, synthetic proteins), and any other suitable moiety. In a specific example, the particle shell of the glass microbubbles can be coated with an aminosilane layer to allow for subsequent surface functionalization with biomolecules (e.g., antibodies, aptamers, lectins, oligos, etc.). After glass microbubbles have been amino-functionalized, the glass microbubbles are preferably crosslinked to streptavidin. However, any other suitable chemical procedure can be performed for surface functionalization of the substrates (e.g., PEGylation, click chemistry, layer-by-layer assembly, ink-jet printing etc.) for selective capture of target constituents, using any other suitable moiety.

In another variation, substrates can additionally and/or alternatively function as a signal delivery agent to target constituents (e.g., via a recombinant molecule bound to the surface of the substrate particle). In a specific example, CD3+ T cells can be captured using a microbubble displaying Cd28, a protein which can stimulate the T cell (e.g., inducing cell proliferation and cytokine production), a primary step to manufacturing T cells expressing a chimeric antigen receptor (e.g., CAR-T cells) used in cell therapy (e.g., cancer treatment). However, the substrates can be otherwise configured with any other suitable moiety for multifunctional applications including target-bound complex separation and extraction.

Preferably, combining the volume of substrates (substrate volume) with the sample containing the target constituent (target sample volume) in Block S110 is performed in a manner that provides sufficient combination and dwell time to achieve sufficient complexification (i.e., forming of complexes) of the target constituent to the substrate particle (e.g., with a desired binding efficiency). In solution (e.g., PBS, water, RPMI, etc.), the initial concentration of the substrates within the volume of substrates, prior to combination of the substrate volume and the target sample volume, is preferably 40 to 125 million substrate particles per mL, but can be any other suitable concentration. The complexification binding efficacy can be dependent on the volume ratio of buoyant particles to target constituent in the total sample volume (combined sample volume). In a specific example, complexification with a binding efficiency of 90% can occur in a buffer solution that includes at least one of PBS, EDTA, and BSA wherein the volume ratio of buoyant particles to target constituent is 1:2, with a dwell time of 20 minutes. In a second specific example, complexification with a binding efficiency of up to 98% binding efficiency can occur in a buffer solution that includes at least one of PBS, EDTA, and BSA wherein the volume ratio of buoyant particles to target constituent is 3:1, with a dwell time of 20 minutes. However, any suitable combination of substrate, target constituent, solvent, and/or additional binding agents and respective dwell times can be used in any other suitable manner to achieve any value of complexification binding efficacy.

After combination of substrates and target constituents in Block S110, the final concentrations of substrate particles, final concentration of target constituents, and the total sample volume in the process chamber can vary depending on the type of target constituent (e.g., red blood cell, white blood cell, T cells, B Cells, etc.), the percentage composition of the target constituent in the target sample (e.g., T Cells can make up to approximately 50% of cells in a human peripheral blood mononuclear cell sample), the total number of target constituents, the rate of complexification, the buffer used in the target sample solution containing the target constituents, and/or any other suitable factor. For example, an initial target sample concentration of 40,000 cells per microliter fluidic volume can be processed (e.g., captured and separated) by obtaining (e.g., by dilution) a final total sample concentration, wherein the final substrate concentration ranges from 7,400 to 55,000 substrate particles per microliter and the final target constituent concentration ranges from 18,000 to 37,000 cells per microliter. In another example, an initial target sample concentration of 200,000 cells per microliter fluidic volume can be processed by obtaining a final total sample concentration wherein the final substrate concentration ranges from 25,000 to 90,000 substrate particles per microliter and the final target constituent concentration ranges from 29,000 to 145,000 cells per microliter. However, the final concentrations of each of the substrate particles, the target constituents, target-bound complexes, and/or any other component of the total sample can be otherwise configured.

In Block S110, combination of the substrate volume with the target sample volume is preferably achieved using trituration methods; however combination can be achieved by end over end rotation, shaking, and/or any other suitable method to thoroughly combine the substrate volume with the target sample volume for complexification. In a variation, trituration is used to combine the substrate volume with the target sample volume, using a pipette (e.g., syringe, pump, hydraulic device, etc.) configured to transfer (e.g., add, remove) up to 50-100% of the fluidic volume from the process chamber up to 60 repetitions. However, combining the substrate volume and the target sample volume can be achieved in any other suitable manner.

Furthermore, combination in Block S110 is preferably performed in a manner that prevents damage to (e.g., due to shear forces, due to other forces) or destruction of substrates of the volume of substrates and/or elements of the target constituent. In one variation, the target sample volume can include a buffer solution configured to provide a biocompatible (e.g., non-toxic, non-hazardous) environment for target constituents. In a specific example, buffer solution includes at least one of PBS, BSA, and/or EDTA. In another variation, the target sample volume can include a buffer solution configured to maintain the stability of the substrate particles and includes at least a combination of PBS, EDTA, and NaCl. However, the buffer solution can include any other suitable reagent, growth factor, chemical compounds, solvent, and/or be of any suitable pH, temperature, or other characteristic to support the viability of substrate particles (e.g., minimize particle aggregation, improve longterm storage, etc.) and/or target constituents. Additionally, combining in Block S110 can be performed in a manner that prevents foaming of sample volumes, which can impede separation of the target constituent from the sample in subsequent blocks of the method according to buoyancy-based approaches. For instance, combining in Block S110 can be performed with a characteristic velocity (e.g., linear velocity, angular velocity) and/or below a desired level of acceleration of the process chamber in order to prevent foaming of the sample. However, combining in Block S110 can additionally or alternatively be performed in a manner that facilitates lysing of sample components (e.g., non-target sample components, target sample components where lysing releases the target constituent for binding to the volume of substrates). For instance, mixing to lyse untargeted sample components can facilitate subsequent separation of the untargeted sample components from the target constituents of the sample. Additionally or alternatively, lysing portions of the sample can facilitate release of the target constituent into solution for binding to the volume of substrates. However, combining in Block S110 can alternatively be performed in any other suitable manner.

In variations for multiplex separation and/or processing of a set of target constituents of the sample, the volume of substrates used in Block S110 can additionally or alternatively be configured to selectively bind to one of a set of target constituents of the sample. In one variation, the volume of substrates can comprise a first subset of substrates having a first density and processed with a first moiety configured to target a first target constituent, a second subset of substrates having a second density and processed with a second moiety configured to target a second target constituent, and any other suitable number of subsets of substrates having distinguishable densities and processed with specific moieties for targeting any other suitable number of target constituents of the sample. In one such example, the volume of substrates can include a first subset of substrates having a first density and processed with a moiety for targeting CD133+ expressing cells, a second subset of substrates having a second density (different form the first density) and processed with a moiety for targeting CD15+ expressing cells, and a third subset of substrates having a third density (different from the first and the second densities) and processed with moieties for targeting CD133+ and CD15+ expressing cells. In the example, specific subsets of the set of substrates can thus facilitate selective separation of cells expressing different biomarkers for further analysis. However, alternative variations of the volume of substrates can include subsets of substrates having any other features (e.g., physical feature, chemical feature, etc.) and configured to bind to different target constituents of the sample, in order to facilitate selective separation of different target constituents from the sample. Furthermore, in some variations, at least a subset of the volume of substrates can be configured to bind to and facilitate separation of an untargeted (e.g., waste, debris, etc.) portion of the sample.

In Block S110, combining can be supported by or supplemented with provision of environmental conditions and/or additional process reagents, to support subsequent processing steps and/or analysis of the target constituent. In one variation, mixing can be supplemented with modulating a temperature within the process chamber (e.g., to facilitate lysis or binding of the target constituent to the volume of substrates, to thermocycle the sample, etc.). Additionally or alternatively, mixing can include providing a lysing reagent (e.g., lysing solution, bead beating solution, etc.) within the process chamber, along with the sample and the volume of substrates, in order to facilitate lysis of undesired constituents of the sample and/or lysis of portions of the sample to release the target constituent for binding to the volume of substrates. Additionally or alternatively, mixing can include providing a fixing reagent (e.g., a cross-linking reagent) configured to fix portions of the sample. Additionally or alternatively, mixing can include providing a pH modulating reagent within the process chamber, and/or any other suitable reagent configured to provide a desired environment within the process chamber. However, Block S110 can be performed using any other suitable combination of reagents and/or adjustments to temperature, pH, or composition.

1.2 Method—Washing and Separation

Block S120 recites: within the process chamber, physically separating the population of target-bound complexes from the sample based upon interaction between the volume of substrates and an applied force. Similar to Block S110, Block S120 is preferably performed within an embodiment, variation, or example of the process chamber described in Section 2 below; however, Block S120 can additionally or alternatively be performed using any other suitable process chamber. Furthermore, while Blocks S110 and S120 are preferably implemented within the same process chamber, Blocks S110 and S120 can alternatively be implemented using separate process chambers.

Block S120 functions to enable distinction of the population of target-bound complexes from other portions of the sample. In Block S120, physical separation can include promoting passive buoyant separation, within the process chamber, whereby the population of target-bound complexes experience buoyant forces due to effects of gravitational force on the volume of substrates having the first density, different from the densities of other untargeted constituents of the sample. Thus, a gravitational force can allow the population of target-bound complexes to move opposite a direction of the gravitational force for collection in Block S130. Additionally or alternatively, in Block S120, physical separation can include promoting active buoyant separation, within the process chamber, whereby the population of target-bound complexes experience buoyant forces due to effects of centrifugal force about an axis of rotation of the process chamber (e.g., as applied by a centrifuge interacting with the process chamber). Implementing active buoyant separation can further increase a separation effect over that of passive buoyant separation alone. Embodiments, variations, and/or examples of Block S110 are further described in U.S. application Ser. No. 14/969,446, filed 15 Dec. 2015.

In relation to separation in Block S120, embodiments of the method 100 can additionally or alternatively include Block S122, as shown in FIG. 1B, which recites: within the process chamber, washing the population of target-bound complexes. Block S122 functions to facilitate purification and/or enrichment of the population of target-bound complexes within the process chamber, prior to extraction of the population of target-bound complexes from the process chamber in subsequent blocks of the method 100. As such, Block S122 can facilitate removal of the non-target constituents of the sample in promoting a higher degree of efficiency in extraction of the target constituent from the sample.

Figure 1D:
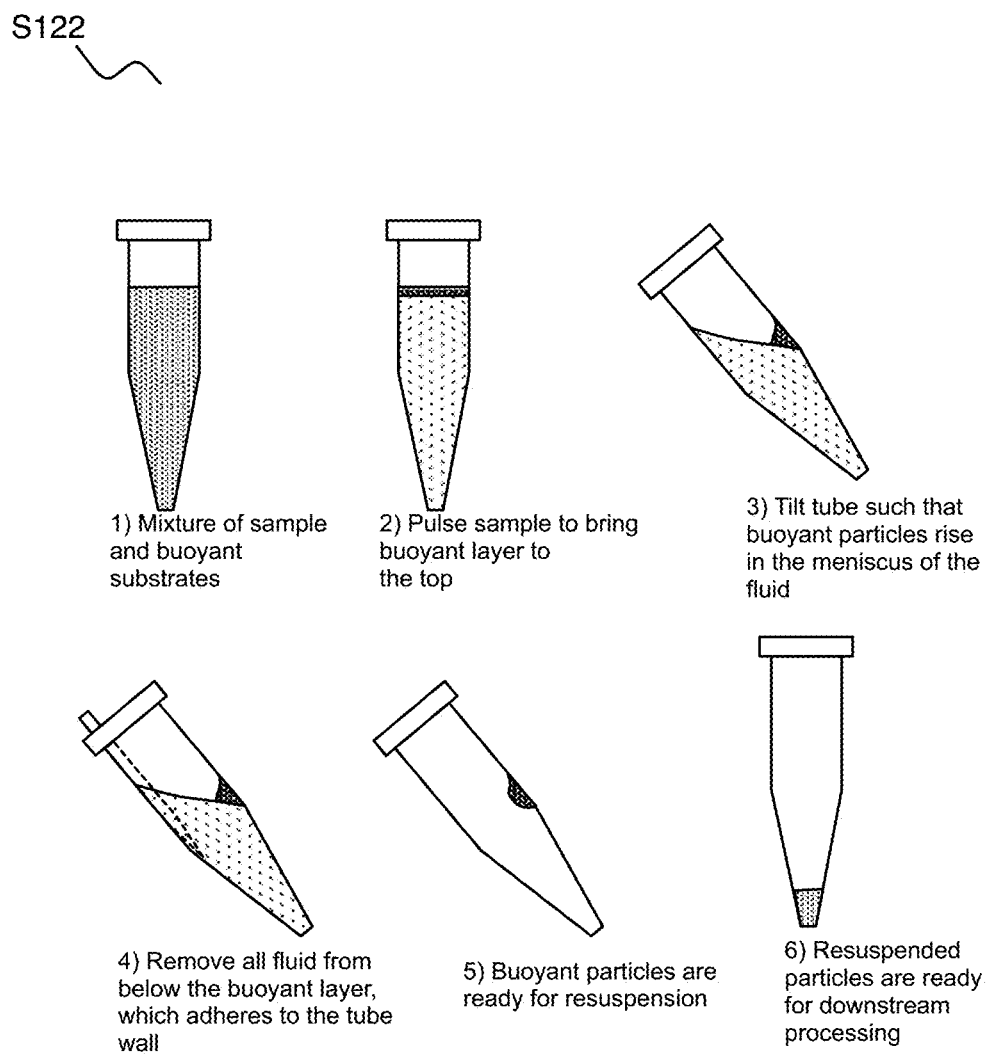
FIG. 1D depicts an example of a block of an embodiment of a method for buoyant separation of a target constituent of a sample.

Preferably, as shown in FIGS. 1B and 1D, Block S122 includes bringing the population of target-bound complexes to a desired region of the process chamber with an applied force; adjusting an orientation of the process chamber, thereby promoting the population of target-bound complexes to adhere to a wall of the process chamber; removing non-target portions of the sample from the process chamber; and resuspending the population of target-bound complexes within the process chamber with a suspension volume of fluid having a sufficiently high density. Washing in Block S122 can be performed any suitable number of times prior to extraction of the population of target-bound complexes in subsequent blocks of the method 100.

In Block S122, bringing the population of target-bound complexes to a desired region of the process chamber with an applied force can include allowing the population of target-bound complexes to undergo passive buoyant separation, within the process chamber, whereby the population of target-bound complexes experience buoyant forces due to effects of gravitational force on the volume of substrates having the first density, different from the densities of other untargeted constituents of the sample. Thus, a gravitational force can allow the population of target-bound complexes to move opposite a direction of the gravitational force in support of the washing operation of Block S122. Additionally or alternatively, in Block S122, physical separation can include promoting active buoyant separation, within the process chamber, whereby the population of target-bound complexes experience buoyant forces due to effects of centrifugal force about an axis of rotation of the process chamber (e.g., as applied by a centrifuge interacting with the process chamber). Additionally or alternatively, physical separation can be implemented in any other suitable manner.

In Block S122, adjusting an orientation of the process chamber, functions to allow the population of target-bound complexes to adhere to a wall of the process chamber. In more detail, tilting of the process chamber can allow the population of target-bound complexes to aggregate at an anti-dependent rim of a fluid meniscus formed within the process chamber (e.g., an upper rim of a fluid meniscus in the orientation shown in FIG. 1D), after which removal of non-target portions of the sample from the process chamber can be performed (e.g., by pipetting, etc.). Thus, with gentle aspiration, non-target components of the sample, as well as a bulk of the sample fluid, can be removed from the process chamber while a substantially purified volume of the population of target-bound complexes is retained at the wall of the process chamber. Finally, the population of target-bound complexes can be washed from the wall of the process chamber and resuspended within a volume of fluid, where the volume of fluid is similar to, greater than, or substantially smaller than the original volume of fluid in the sample.

Additionally or alternatively, to enhance retention of the population of target-bound complexes at the process chamber during the washing process of Block S122, interior surfaces of the process chamber, proximal the collection region(s), can be patterned (e.g., roughened, texturized by etching, textured by molding, tapped/threaded, etc.) to enhance retention of the population of target-bound complexes at desired regions of the process chamber, as described in Section 2 below. Additionally or alternatively, retention of the target-bound complexes at regions of the process chamber can be enhanced by utilizing a recessed region or other region of the process chamber defining a separated interior volume of the process chamber, configured to retain the population of target-bound complexes during washing. Additionally or alternatively, washing in Block S122 can be enhanced by including a high molecular weight polymer with a washing solution, thereby promoting the generation of colloidal forces to reversibly enhance aggregation of the population of target-bound complexes within the fluid meniscus of the process chamber.

Block S122 can be performed manually (e.g., by an technician or other entity), or can alternatively be performed in an automated manner (e.g., with an automated system for adjusting the orientation of the process chamber, and with a fluid handling system for aspirating the non-target components of the sample/washing the target components of the sample). Block S122 can, however, be performed in any other suitable manner.

1.3 Method—Aggregation at a Collection Region

Block S130 recites: aggregating the population of target-bound complexes at a collection region of the process chamber, which functions to aggregate the population of target-bound complexes to at least one desired region of the process chamber, in order to facilitate extraction of the target constituent from the sample in an efficient manner. Interactions (e.g., hydrophobic interactions, hydrophilic interactions, neutral interactions) between fluid of the sample and the process chamber, and/or the method of separation (e.g., passive buoyant separation, active buoyant separation, compound density gradient, etc.) can affect the location(s) of the collection region(s) of the process chamber at which the population of target-bound complexes reside. Embodiments, variations, and/or examples of Block S110 are further described in U.S. application Ser. No. 14/969,446, filed 15 Dec. 2015.

In some variations, implementation of passive buoyant separation in Block S120 can provide one or more collection region profiles, depending upon interaction of the process chamber with fluid of the sample. As shown in FIG. 2A, in variations of Block S120 that include a hydrophilic interaction between fluid of the sample and the process chamber, a concave meniscus formed at the fluid surface can provide a collection region at the perimeter of the fluid surface (e.g., a circular annular collection region for a cylindrical process chamber, a rectangular annular collection region for a rectangular prismatic process chamber, etc.) where clearing or an otherwise lower density population of target-bound complexes within the center of the meniscus can be used to extract bulk sample fluid and leave the population of target-bound complexes within the process chamber. However, as shown in FIG. 2B, the meniscus can also be convex, wherein a higher density population of target-bound complexes occurs within the center of the fluid surface, allowing extraction of the target-bound complexes away from the collection region at the center of the process chamber. As shown in FIG. 2C, in variations of Block S120 that include a neutral (e.g., non-hydrophobic, non-hydrophilic) interaction between fluid of the sample and the process chamber, a substantially planar surface formed at the fluid surface can provide a collection region at the fluid surface. Examples of process chambers contributing to a concave or a convex fluid meniscus associated with a sample volume can include one or more of: a microwell plate, a microfabricated array, any other suitable well plate, any other suitable fabricated array, and any other suitable process chamber. Furthermore, as shown in FIG. 2D, the use of various reagents (e.g., water, PBS, RPMI, with or without protein additives) can be used to influence the shape of the fluid meniscus. In more detail, the shape of the meniscus can be influenced by the interaction of the well plate (e.g., material composition, surface treatments, sidewall features, morphological characteristics) with the sample fluid within the well, and additionally and/or alternatively can be modified by combining various buffers (e.g., containing different solutions, salts, surfactants, etc.) within the total sample volume (e.g., to influence surface tension of the sample fluid). However, any suitable reagent and/or solvent can be used to perform Block S130 and/or any other portion of method 100.

Figure 3A:
FIGS. 3A-3D depict variations of a process chamber morphological configurations in embodiments of a system and method for buoyant separation of a target constituent of a sample.
Figure 3B:
Figure 3D:
Figure 3C:
Figure 4:
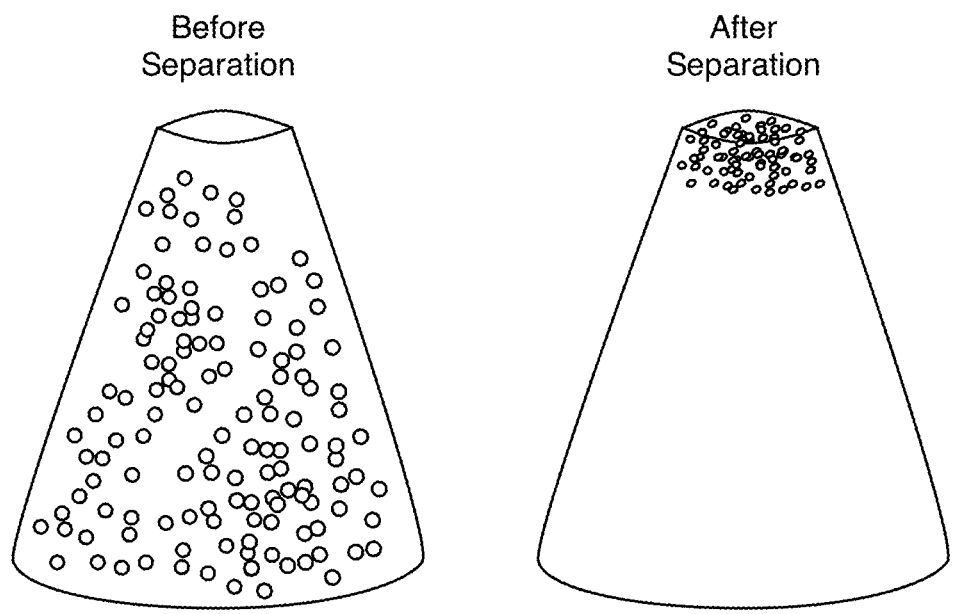
FIG. 4 depicts a specific example of a process chamber used in an embodiment of a method for buoyant separation of a target constituent of a sample.
Figure 5:
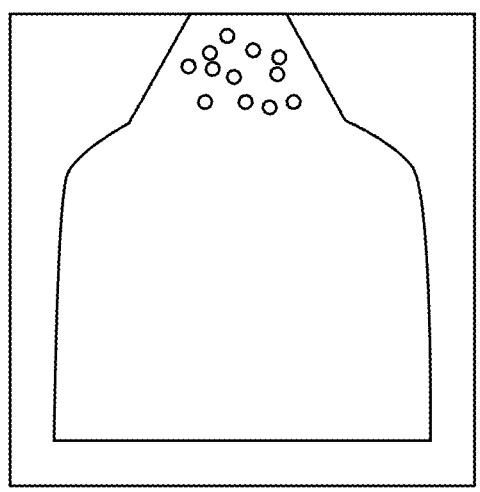
FIG. 5 depicts a specific example of a process chamber used in an embodiment of a method for buoyant separation of a target constituent of a sample.

In any of the above variations, morphology and/or concentration of the collection region(s) can be enhanced by providing process chamber morphologies that affect the morphology(ies) of the collection region(s). For instance, in the examples shown in FIGS. 3A-3D, a conical process chamber morphology (e.g., linear conical, curved conical, etc.) with the vertex oriented at a superior portion of the process chamber can concentrate the collection region to a smaller region in comparison to a process chamber having a substantially constant or widening cross-section (i.e., in an inferior to superior direction) along a longitudinal axis of the process chamber. In one example, as shown in FIG. 4, a frustoconical process chamber having a vertex oriented at a superior portion of the process chamber can concentrate the collection region, and an opening at the vertex of the frustoconical process chamber can enhance separation and facilitate collection of the population of target-bound complexes at the opening. Furthermore, overfilling of the frustoconical process chamber with the sample can provide a convex fluid surface at the opening, in the example, that effectively concentrates the population of target-bound complexes to a single location for extraction in Block S140. However, any other suitable morphology of process chamber, another example of which is shown in FIG. 5, can be used to produce any shape of collection region and/or any number of collection regions within a process chamber. Furthermore, interior surface features of the process chamber can enhance collection in Block S130, as described in Section 2. In one example, a process chamber that has one or more recessed regions (e.g., scoring lines) at given positions (e.g., heights) along its interior surface (e.g., sidewall) can facilitate collection of the population of target-bound complexes within the recessed region(s) for later extraction in Block S140. In this example, the recessed regions can facilitate repeated separation and washing of the population of target-bound complexes within the process chamber. In a specific example, a 1.5 mL centrifuge tube used as the process chamber can be tapped, wherein a set of internal threads along the sidewall of the centrifuge tube can be formed using an M9-sized tap or any other suitable tool (e.g., spiral flute tap, spiral point tap, pin, plug, etc.). The modified (e.g., threaded) sidewalls of the centrifuge tube can then be used to efficiently capture target-bound complexes around the entire circumference and upper section of the tube (e.g., due to surface tension between the sample fluid and the set of internal threads of the sidewall), However, the process chamber can be otherwise modified and/or configured as described in Section 2.

In a specific example, aggregating the population of target-bound complexes can comprise aggregating the population of target-bound complexes at a superior portion of a process chamber (e.g., at a liquid-air interface of a sample volume within the process chamber), based upon passive buoyant separation. However, variations of the example can comprise any other suitable region for aggregation.

Figure 6A:
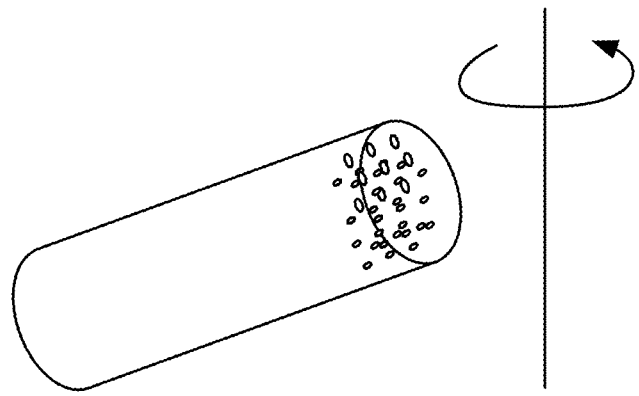
FIGS. 6A-6B depict variations of collection regions, dependent upon rotation axis, in an embodiment of a method for buoyant separation of a target constituent of a sample.
Figure 6B:
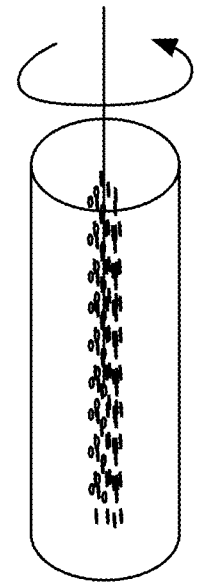
Figure 7A:
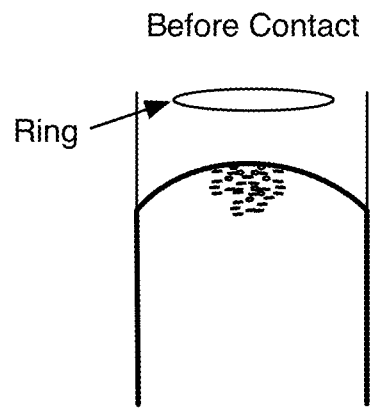
FIGS. 7A-7B depict a variation of extraction in an embodiment of a method for buoyant separation of a target constituent of a sample.
Figure 7B:
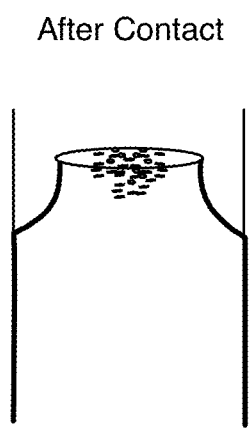

In variations of Block S120 implementing an active buoyant separation process, an axis or point about which the process chamber rotates governs the location of the collection region in Block S130. In particular, the population of target-bound complexes and/or substrates of the volume of substrates will migrate in a direction opposite that of a centrifugal or gravitational force. In one variation, wherein the process chamber rotates about a radial axis, as shown in FIG. 6A, lower density particles (e.g., particles of the population of target-bound complexes, substrates of the volume of substrates) in the sample move toward the radial axis and higher density particles move away from the radial axis. As such, the collection region in this variation is positioned at the portion(s) of the process chamber that were closest to the radial axis during rotation of the process chamber about the radial axis. In another variation, wherein the process chamber rotates about a longitudinal axis of the process chamber, as shown in FIG. 6B, lower density particles (e.g., particles of the population of target-bound complexes, substrates of the volume of substrates) in the sample move toward the longitudinal axis and higher density particles move away from the longitudinal axis. As such, the collection region in this variation is positioned at the portion(s) of the process chamber that were closest to the longitudinal axis during rotation of the process chamber about the longitudinal axis. Furthermore, in variations wherein rotation occurs about a longitudinal axis of the process chamber, a rate at which lower density particles float can be increased due to enhancement of buoyant effects resulting from increased proximity between multiple low density particles.

Figure 1E:
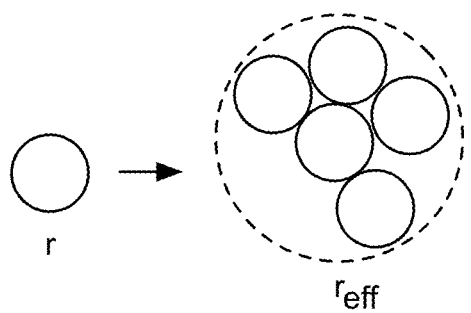
FIGS. 1E-1I depict an example of a block of an embodiment of a method for buoyant separation of a target constituent of a sample.
Figure 1F:
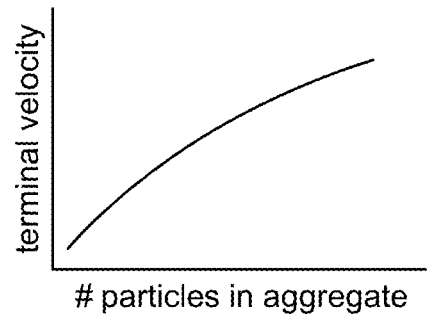

In more detail, and in relation to either passive or active buoyant separation, Block S130 can include enhancing a speed at which aggregation occurs by promoting a reduction in proximity between complexes of the population of target-bound complexes. As such, the method 100 can include Block S135, as shown in FIG. 1B, which recites: transitioning the process chamber into a first orientation that promotes an increase in a complex-to-complex proximity metric for the set of target-bound complexes. Block S135 can function to increase an effective radius, $r_{eff}$, and therefore, to increase an effective volume of aggregates of the population of target-bound complexes, thereby increasing the effective buoyant forces on aggregates of the population of target-bound complexes. As shown in FIG. 1E, as the number of buoyant particles within an aggregate increases, the net buoyant force, and therefore the terminal velocity of the aggregate increases, thereby enhancing a speed at which aggregation occurs.

Figure 1G:
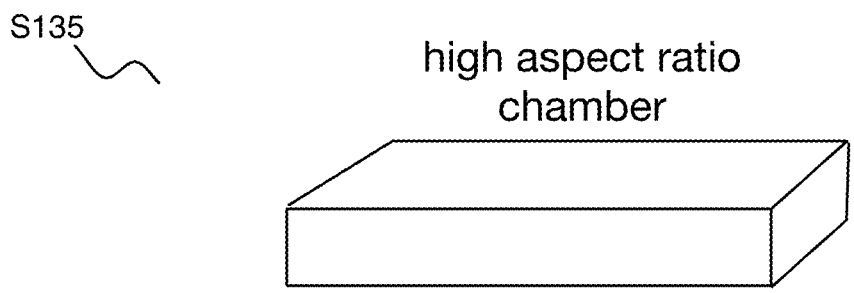
Figure 1H:
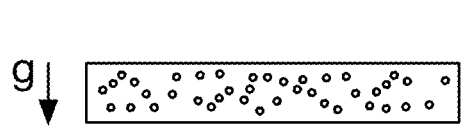
Figure 1H:
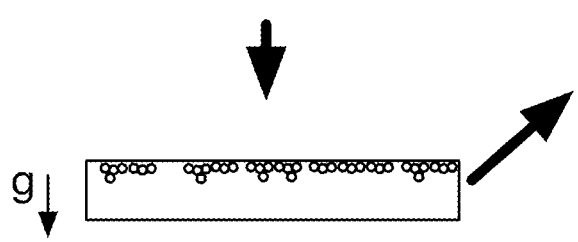
Figure 1I:
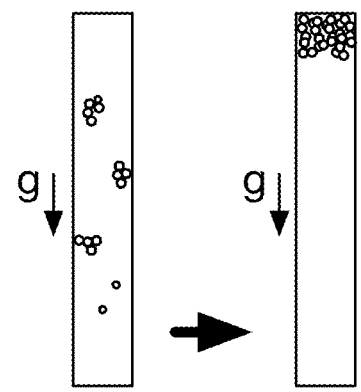

In one variation, as shown in FIGS. 1G-1I, Block S135 can include implementing a process chamber that has a high aspect ratio (e.g., rectangular prism), wherein the process chamber is transitioned into a first orientation that promotes an increase in a complex-to-complex proximity metric for the set of target-bound complexes (e.g., the process chamber is transitioned onto its side). In this variation, the first orientation can be associated with an orientation wherein a short axis of the process chamber is substantially aligned with a direction of gravity. Maintenance of this orientation for a duration of time thus allows buoyant particles to move through the shortest possible distance in forming aggregates. Then, Block S135 can include transitioning the process chamber from the first orientation to a second orientation that drives the set of target-bound complexes toward a collection region of the process chamber. The second orientation can be associated with an orientation wherein a long axis of the process chamber is substantially aligned with a direction of gravity. This orientation thus allows the formed aggregates to aggregate toward the collection region of the process chamber in a manner that is more rapid than that of individual buoyant particles, due to a combination of hydrodynamic drafting among buoyant particles and the formation of transient particle aggregates with a much greater effective volume.

Figure 1J:
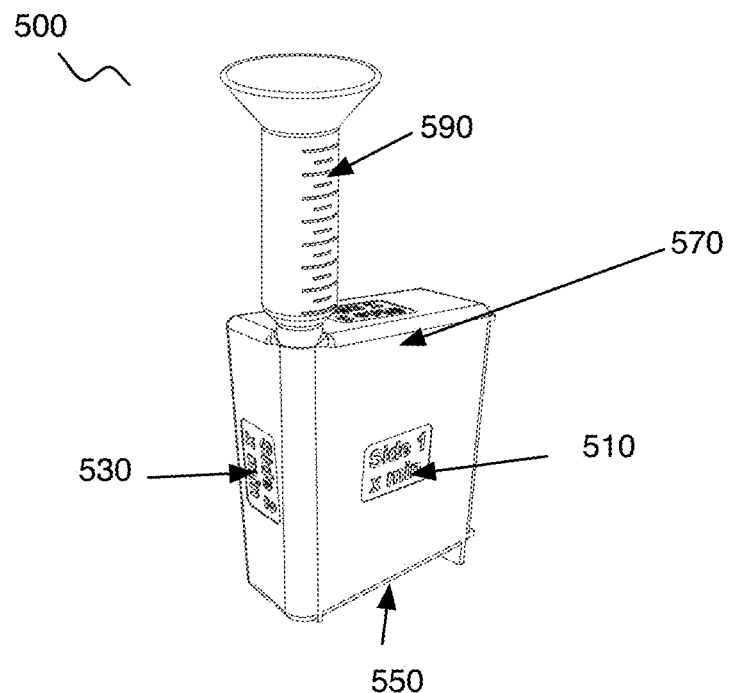
FIG. 1J depicts a specific example of a process chamber used in embodiments of a system and method for buoyant separation of a target constituent of a sample.
Figures 1K, 1L, 1M:
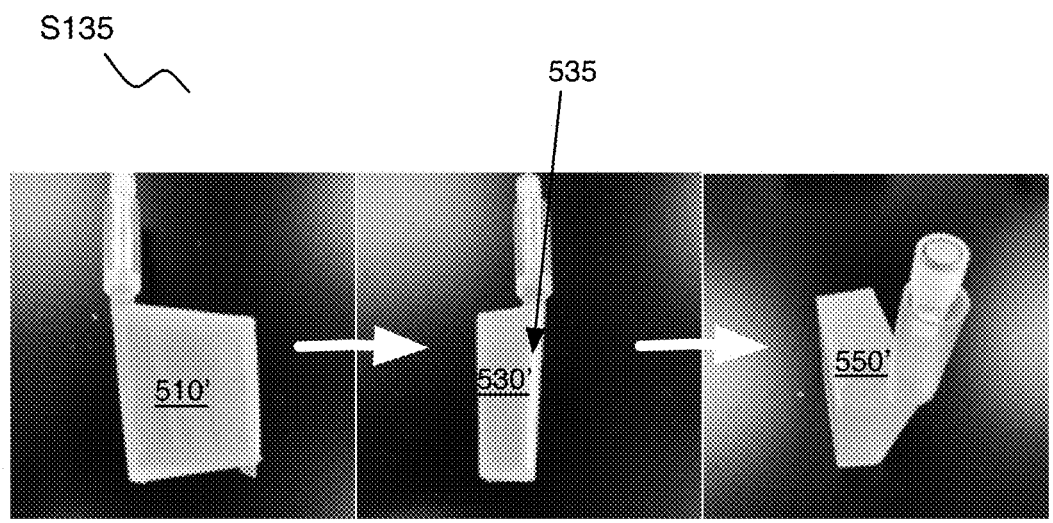
FIGS. 1K-1M depict a specific example of a block of an embodiment of a method for buoyant separation of a target constituent of a sample.

In a specific example, as shown in FIG. 1J and FIGS. 1K-1M, a rectangular process chamber 500 can be used to improve the speed of separation of target-bound complexes from a large volume of solution (e.g., 25 mL, 100 mL, 1000 mL, etc.). The rectangular process chamber 500, further described in Section 2, includes a rectangular prismatic morphology having a high aspect ratio (e.g., vertical height is greater than the width) with walls configured at an angular offset from vertical (e.g., 1°, 3°, 5°, 15°, etc.). As shown in FIGS. 1K-1M, after the sample is added to the rectangular process chamber, separation can occur in three steps, wherein each step can include turning the process chamber onto one of three exterior surfaces with a respective dwell time (e.g., 1-20 minutes duration on each side) for each step, thus concentrating the target-bound complexes against an opposing interior sidewall, edge of a sidewall, and/or any other suitable surface of the process chamber. In a first step (FIG. 1K), the rectangular process chamber 500 can rest on its broad surface 510, allowing the target-bound complexes to rise to the opposing first sidewall 510'. In a second step (FIG. 1L), the rectangular process chamber 500 is rotated about its longitudinal axis by 90° to rest on its side surface 530, thus allowing the target-bound complexes to aggregate against the sidewall edge 535 between the first sidewall 510' and a second sidewall 530' opposing the side surface 530. In a third step (FIG. 1M), the rectangular process chamber 500 is rotated about its horizontal axis by 90°, bringing the rectangular process chamber 500 into its upright position, and enabling increased velocity of the target-bound complexes to the collection region 570 (e.g., upper region of the process chamber 500), due to the improved complex-to-complex proximity metric of buoyant particles at the sidewall edge in the second step. However, adjusting the orientation of the process chamber can be performed in any other suitable manner, with any number of steps, and/or with any other rate of transition between orientations (e.g., fixed steps, constant rotation, rapid movements, multiple axes, etc.) in order to efficiently separate the target-bound complexes from solution.

In other variations, Block S135 can additionally or alternatively include actively forming aggregates of subsets of the population of target-bound complexes based upon one or more of: centrifugation of the process chamber about any suitable axis; binding of multiple buoyant substrate particles to each unit of the target constituent of the sample; use of high-molecular weight polymer solutions that promote aggregation of the population of target-bound complexes in a reversible manner; and any other suitable means to promote aggregation. In relation to binding of multiple buoyant substrate particles to each unit of the target constituent of the sample, binding can be tuned such that rising of an aggregate within the process chamber only occurs when a desired number of buoyant components (e.g., 2 or more buoyant substrates) are coupled to a target. However, variations of Block S135 can additionally or alternatively be implemented in any other suitable manner. Furthermore, in any of the above variations of separation, separation can be used to indicate presence of the target constituent (e.g., using natural coloring of the target constituent, using stains, etc.), whereby monitoring of completion of a binding process based on completeness of a band of separation can additionally or alternatively be implemented.

1.4 Method—Extraction

Block S140 recites: extracting the population of target-bound complexes from the process chamber, which functions to remove the population of target-bound complexes from other portions of the sample, or to remove portions of the sample from the population of target-bound complexes, thereby generating an enriched volume comprising the population of target-bound complexes. Block S140 preferably includes transmitting a target constituent extractor into the process chamber, concentrating the population of target-bound complexes at a region of the target constituent extractor, and delivering the population of target-bound complexes from the target constituent extractor for downstream processing. Embodiments, variations, and/or examples of Block S110 are further described in U.S. application Ser. No. 14/969,446, filed 15 Dec. 2015.

In one variation, as described in more detail in Section 2 below, the target constituent extractor can include opposing frustoconical surfaces (FIGS. 15A-15D) configured to facilitate concentration and extraction of the population of target-bound complexes from the process chamber. However, the target constituent extractor can alternatively include a single frustoconical surface facing the surface of the sample fluid, and/or be otherwise configured as described in Section 2. In one example of this variation, the target constituent extractor can include a threaded region that complements threads of the process chamber (e.g., a 50 mL tube), such that transmitting the target constituent extractor includes rotating the target constituent extractor relative to the process chamber in order to engage their complementary threads. In another example of this variation, the target constituent extractor may omit threads, transmitting the target constituent extractor into the process chamber can include translating the target constituent extractor concentrically into an opening of the process chamber. Transmitting the target constituent extractor into the process chamber can, however, be implemented in any other suitable manner. Once inserted into the process chamber, the target constituent extractor can be removably secured; however, the target constituent extractor and/or portions thereof can alternatively be fixed in place (e.g., permanently secured), or otherwise configured (e.g., FIGS. 21A-21B).

In relation to the variation described above, concentrating the population of target-bound complexes at a region of the target constituent extractor can include concentrating the set of target-bound complexes at a region of a frustoconical surface of the target constituent extractor, wherein the target constituent extractor has an inverted frustoconical surface opposing and coupled to the frustoconical surface by a channel. Then, to facilitate delivery of the population of target-bound complexes from the target constituent extractor, a fluid level within the inverted frustoconical surface can be adjusted (e.g., by exertion of an applied force, change in pressure, process chamber movement, solution agitation, etc.), in order to bring the population of target-bound complexes into the inverted frustoconical surface for extraction. In one example, the fluid level can be adjusted upon receiving an additional fluid volume into the channel of the target constituent extractor connecting the two frustoconical surfaces, thereby delivering the population of target-bound complexes from the frustoconical surface and into the inverted frustoconical surface by way of the channel. In another example, the fluid level can be adjusted by translating at least a portion of the target constituent extractor deeper into the process chamber, thereby applying a change in pressure configured to alter a volume of air and or/solution within the process chamber to deliver the population of target-bound complexes from the frustoconical surface and into the inverted frustoconical surface by way of the channel. In another example, wherein the process chamber is deformable (e.g., squeezable), the fluid level can be adjusted upon deformation of the process chamber (e.g., squeezing of the process chamber), thereby delivering the population of target-bound complexes from the frustoconical surface and into the inverted frustoconical surface by way of the channel. However, adjusting the fluid level can additionally or alternatively be implemented in any other suitable manner.

Figure 15A:
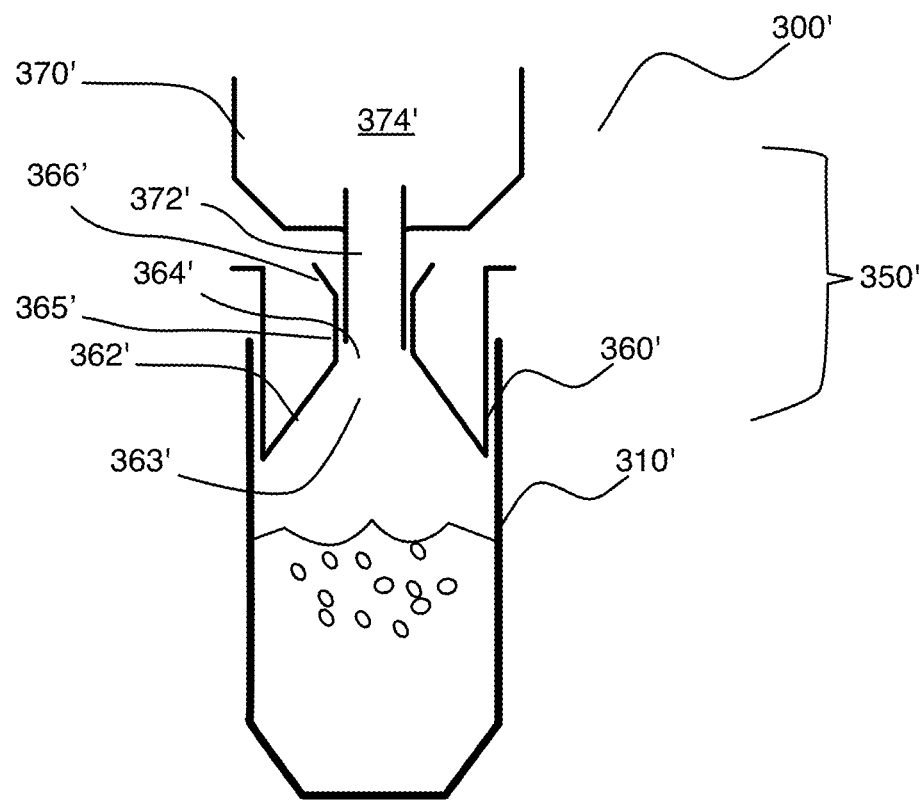
FIGS. 15A-15D depict a variation of an embodiment of a system for buoyant separation of a target constituent of a sample.

Finally, in Block S140, delivering the population of target-bound complexes from the target constituent extractor for downstream processing can include delivering the population of target-bound complexes into a pipette for extraction of the population of target-bound complexes from the target-constituent extractor. Additionally or alternatively, in a variation of the target constituent extractor including a separate extraction component having a second inverted frustoconical surface opposing the inverted frustoconical surface, as shown in FIG. 15A, delivering the population of target-bound complexes can include delivering the population of target-bound complexes into the second inverted frustoconical surface of the separate extraction component (e.g., without involvement of a pipette). Variations of extraction of the population of target-bound complexes can, however, be implemented in any other suitable manner.

Figure 21A:
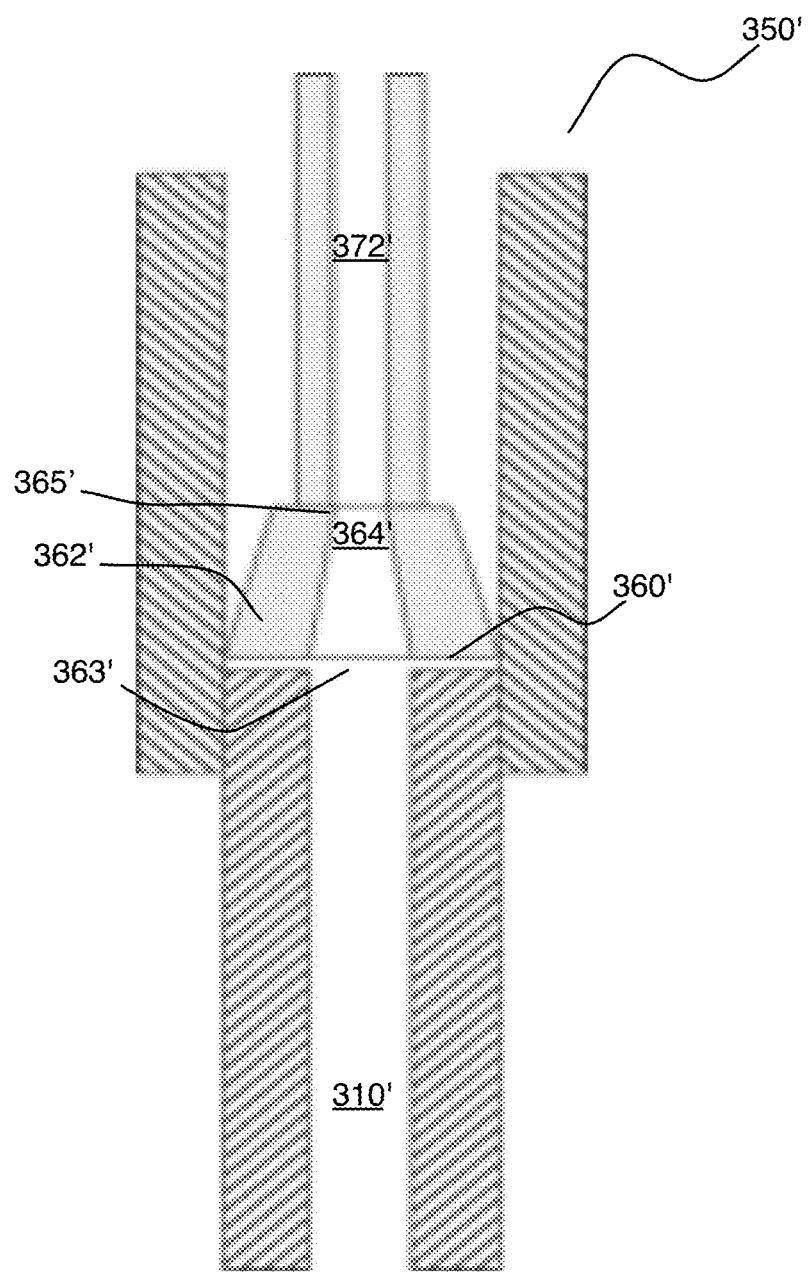
FIG. 21A-21B depict examples of an embodiment of a system for buoyant separation of a target constituent of a sample.
Figure 21B:
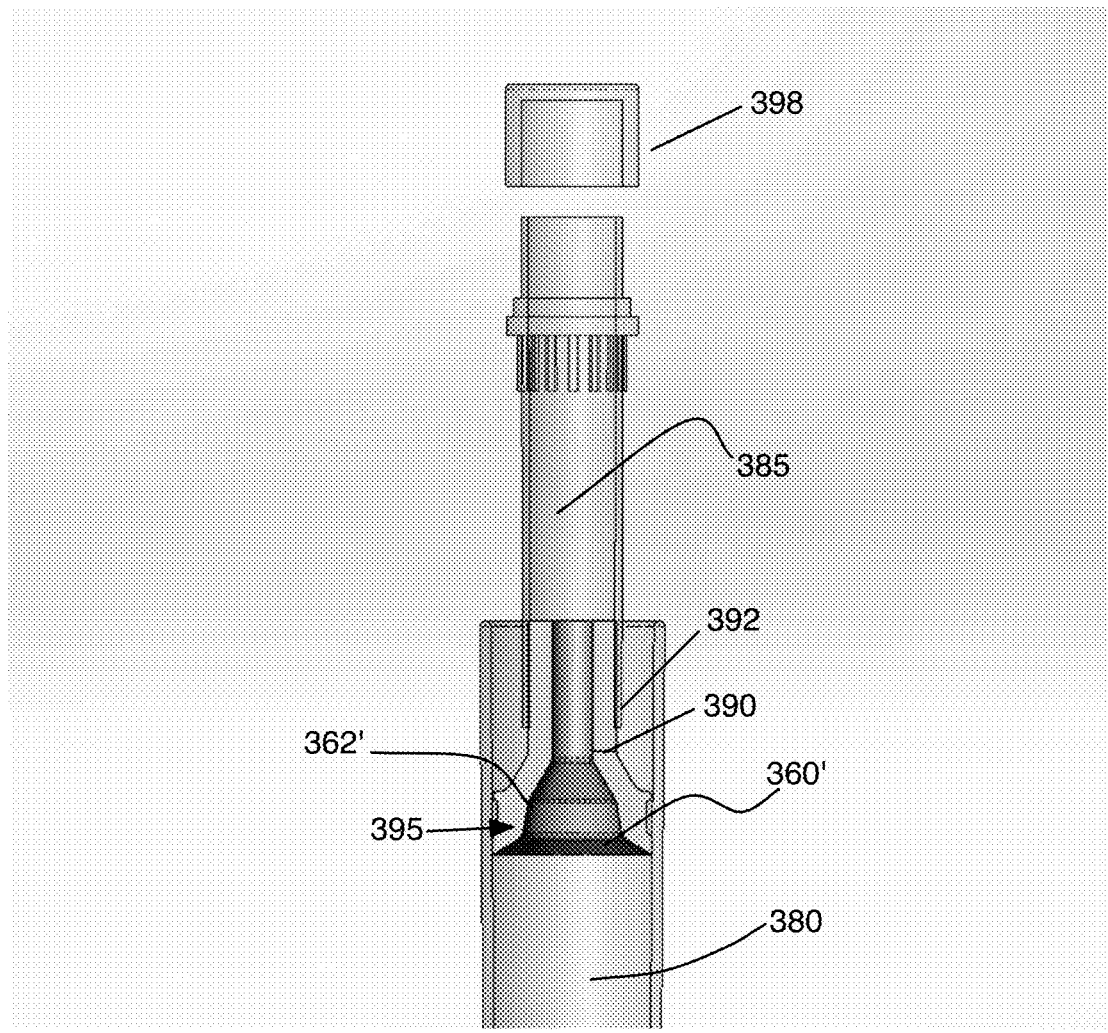

In one embodiment of the system using the variation of the process chamber shown in FIG. 1J and the variation of the extraction apparatus shown in FIGS. 21A-21B, the target constituent extractor can include a continuous fluidic pathway from the process chamber to an upper chamber (e.g., a separate collection tube, secondary container), wherein the upper chamber can be sealed (e.g., to prevent airflow) with a separator lid, such that the target-bound complexes can be maintained in isolation within the upper chamber when the target constituent extractor is completely removed from the process chamber. In one example, as shown in FIG. 21B, a portion of the target constituent extractor (e.g., a frustoconical surface facing the surface of the sample fluid) can be configured as a collection plunger that operates in coordination with a valve slit coupled to a vent path, which regulate the air pressure within the system. When the target extraction apparatus is coupled to the process chamber, the collection plunger can be arranged in a first configuration (e.g., lowered configuration) to enable target-bound complexes to travel into the upper chamber, wherein the valve slit is closed and air is unable to pass through the vent path. Once transfer is complete, the upper chamber can be secured with the separator lid and removed from the sample containing chamber, thus opening the vent path to allow air to pass through the valve slit, maintaining air pressure within either of the upper chamber and the process chamber, such that the fluid in the upper chamber stays in the upper chamber. In one variation, the radius of the opening at $363'$ is configured to be less than the radius of the opening of $364,'$ which functions to allow target-bound complexes to pass from the process chamber to the upper chamber without being caught (e.g., stuck, unflowing, immobile) at the intersection of the two chambers. After target-bound complexes have been recovered in the upper chamber, the extraction apparatus (and the enriched sample captured in the upper chamber) can be removed from the process chamber, whereby the upper chamber can be coupled to a vertically aligned plug inserted into the upper chamber, and/or any other suitable sealing mechanism that fluidly seals the lower portion of the upper chamber, thus allowing the separator lid to be removed from the upper chamber without losing the enriched sample fluid contained in the upper chamber (e.g., due to pressure management within the process chamber and/or upper chamber). However, the extraction apparatus can be otherwise configured.

In removing fluid (e.g., fluid containing the population of target-bound complexes, fluid excluding the population of target-bound complexes) using the target constituent extractor, removal can include active fluid removal (e.g., by pipetting, by capillary action, etc.). Additionally or alternatively, fluid removal can include surface contact methods, whereby an extraction element (e.g., target constituent extractor described below) makes surface contact with fluid of the sample in order to provide extraction. In extraction, fluidic transfer can occur through 1) wetting/capillary forces when an extraction element (e.g., extraction vessel, extraction membrane) makes contact with the collection region containing the population of target-bound complexes and/or 2) further climbing of buoyant elements (e.g., the population of target-bound complexes, substrates of the volume of substrates) within an extraction element. Extraction elements can include one or more of: solid substrates with or without a patterned surface (e.g., a glass substrate with a Teflon pattern to define an active extraction region); capillary structures (e.g., an element with a tubular geometry); annular elements (e.g., a ring, a circular annular element, a rectangular annular element, etc.); and any other suitable element configured to promote fluid transfer.

Figure 8:
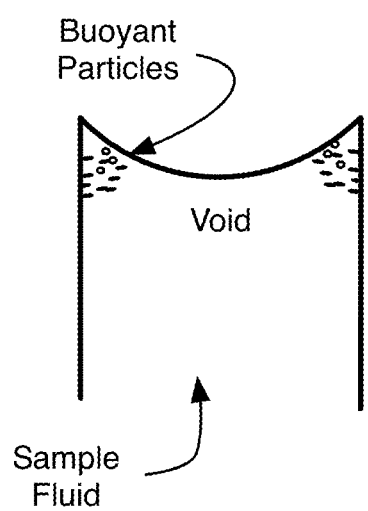
FIG. 8 depicts a variation of extraction in an embodiment of a method for buoyant separation of a target constituent of a sample.

In another example of Block S140 wherein a hydrophilic interaction occurs between fluid of the sample and the process chamber, a region substantially void of the population target-bound complexes can be created proximal a central longitudinal axis of the process chamber, as shown in FIG. 8. In this example, extraction can comprise removal of fluid from the region that is void of the population of target-bound complexes, thus concentrating the population of target-bound complexes within the process chamber. To enhance retention of the population of target-bound complexes at the process chamber and/or the target constituent extractor, interior surfaces of the process chamber and/or portions of the target constituent extractor, proximal the collection region(s), can be patterned (e.g., roughened, texturized by etching, textured by molding, tapped/threaded, etc.) to enhance retention of the population of target-bound complexes at the process chamber, as further described in Section 2. Furthermore, in this example, single-instance or repeated washing (e.g., with a wash buffer) and extraction of fluid from the region that is void of the population of target-bound complexes can further enrich the population of target-bound complexes within the process chamber, as described in relation to Block S122 above. Furthermore, automation of the fluid extraction process (e.g., with an automated liquid handling system) can further remove burden for a technician or other entity associated with the example of Block S140.

While several extraction elements and methods of use are described, any other suitable combination of the above described extraction elements, and/or any other suitable extraction element(s) can facilitate extraction of the population of target-bound complexes in Block S140. Furthermore, while the above Blocks are described in distinction from each other, any one or more of the embodiments, variations, and/or examples of Blocks S110-S140 can be performed substantially simultaneously with each other, in order to provide an efficient sample processing mechanism. As such, in some variations, a process chamber used in the method 100 can be module and comprise a first portion for collection and a second portion for extraction of the population of target-bound complexes, such that collection and extraction can occur simultaneously within a single process chamber. In some variations, the process chamber can further be configured to facilitate simultaneous combination of the volume of substrates with the target constituent, and collection of the population of target-bound complexes, by simultaneously mixing and driving the population of target-bound complexes toward the collection region(s). Simultaneous performance of multiple blocks of the method 100 can, however, be implemented in any other suitable manner.

1.5 Method—Downstream Processing

Block S150 recites: processing the target constituent from the population of target-bound complexes for further analysis. Block S150 functions to provide a means for subsequent processing of the target constituent of the sample for a downstream application. Block S150 can comprise one or more of: Block S160, which recites resuspending the population of target-bound complexes for at least one of analysis and storage; and Block S170, which recites generating an analysis of the target constituent upon processing of the population of target-bound complexes. Embodiments, variations, and/or examples of Block S150, Block S160, and Block S170 are further described in U.S. application Ser. No. 14/969,446, filed 15 Dec. 2015.

In some variations the method 100 can include carrying out surface chemistry and/or other modifications to substrates of the volume of substrates, in order to enhance processing and separation of the target constituent from the sample. Such modifications can be implemented using process chamber morphologies, described further in Section 2 below, which allow multistep modifications to be performed on substrate surfaces without requiring direct handling of the substrates. As such, handling of buoyant substrates can be performed in a manner that reduces product loss and handling of potentially harmful reagents. In one such variation, a process chamber having a dip tube that provides access to fluid within the process chamber, below an active collection region at which buoyant substrates aggregate, can enable fluid transfer in the process chamber substantially without disturbance of the buoyant substrates. In examples, the dip tube can be incorporated into a lid of the process chamber, as shown in FIG. 12A, incorporated into a wall of the process chamber, as shown in FIG. 12B, be a modular component that interfaces with the process chamber (e.g., by adhering to a wall of the process chamber with a membrane), and/or cooperate with the process chamber in any other suitable manner.

1.6 Method—Additional Examples

Figure 10:
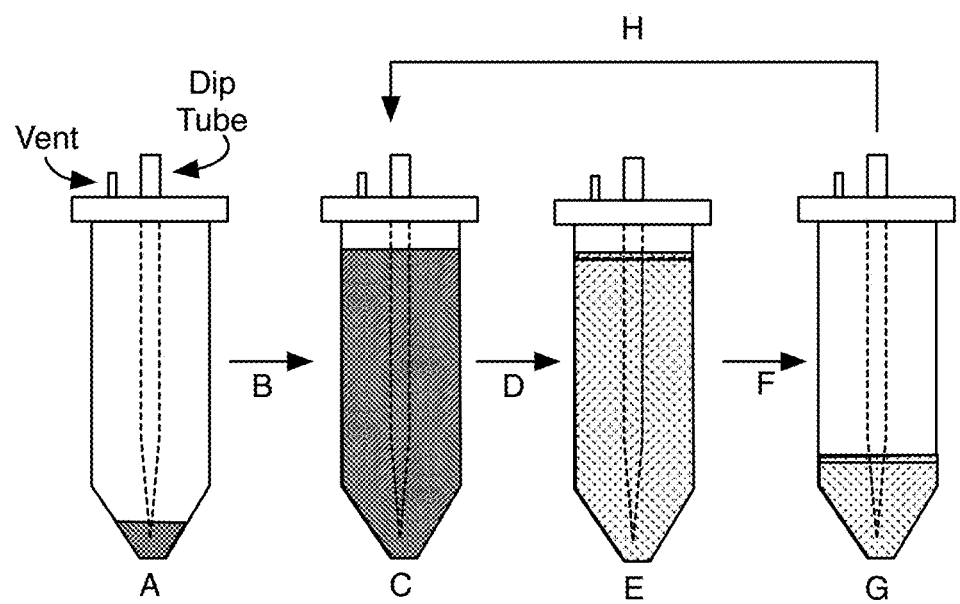
FIG. 10 depicts a variation of a method for substrate modification in a method for buoyant separation of a target constituent of a sample.

In one example workflow for modification of a buoyant substrate, as shown in FIG. 10, the method can include introducing buoyant substrates (e.g., beads in powder form, beads suspended in liquid) into the process chamber (A); adding a first reaction solvent and associated reactants into the process chamber (B), by way of a dip tube coupled to the process chamber (B); incubating the buoyant substrates with the first reaction solvent to achieve chemical modification (C); centrifuging the process chamber (D) to achieve separation of the modified buoyant substrates (E); removing excess portions of the first reaction solvent and reactants from the process chamber, by way of the dip tube (F); preparing the process chamber for additional modification solvents and reactions (G); and repeating steps (A)-(G) as necessary (H).

In a specific example, method 100 can be used to enrich (e.g., separate) murine B cells from splenocytes derived from mice by using the substrate particles to bind to non-target constituents (e.g., non-murine B cells). However, the method 100 can alternatively be used to isolate any other suitable cell type, and the target-bound complexes can include either cells of interest (e.g., to be used for further analysis), cells of non-interest (e.g., to be discarded), and/or any other suitable component of the sample volume. In this example, method 100 includes: at a process chamber, generating a target sample volume including mouse splenocytes at an initial target concentration of $2\times10^6$ cells in 100 μL volume of separation buffer; combining the target sample volume with a substrate volume for a total sample volume of 200 μL, wherein the substrate volume includes an initial substrate concentration of 4 million streptavidin-coated glass microbubbles (e.g., 2 substrate particles per splenocyte); for each process chamber, triturating the sample volume with 60 strokes (1/second for 1 minute); centrifuging the process chamber; and, upon separation of an enriched cell pellet from the microbubbles, aspirating the volume of microbubbles from the upper surface of the sample volume, leaving an enriched murine B cell pellet intact at the base of the tube that can be used for additional processing steps (e.g., for further analysis).

The method 100, can, however, include any other suitable Blocks or Steps for separating a target constituent from a sample based upon buoyancy and/or any other separation mechanism, and generating an analysis based upon processing of the target constituent. Furthermore, as a person skilled in the art will recognize from the previous detailed description and from the figures, modifications and changes can be made to the method 100 without departing from the scope of the method 100.

2. System

2.1 System—Process Chamber

Figure 11:
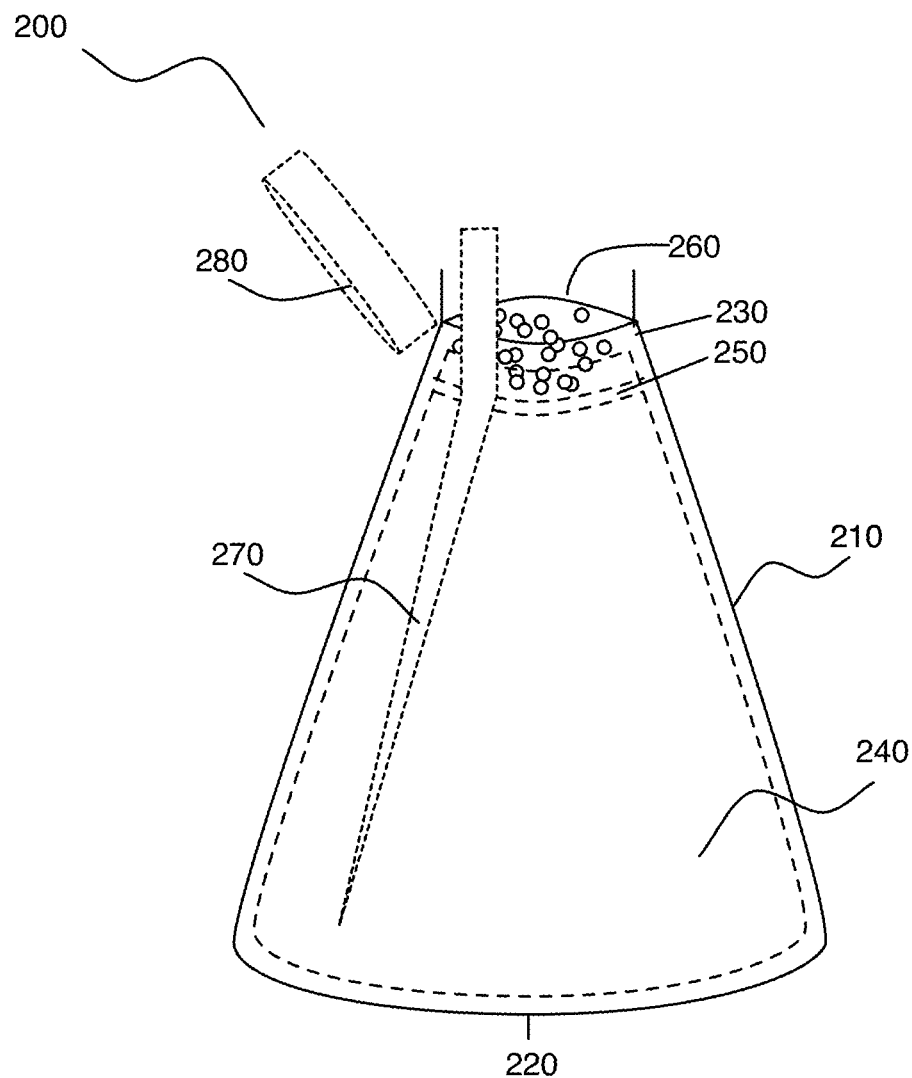
FIG. 11 depicts an embodiment of a system for buoyant separation of a target constituent of a sample.
Figure 14:
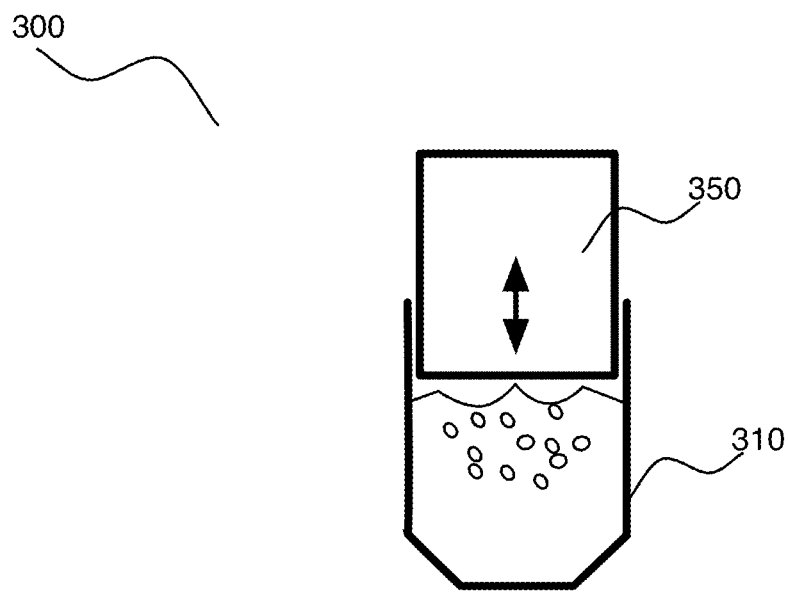
FIG. 14 depicts an embodiment of a system for buoyant separation of a target constituent of a sample.

As shown in FIG. 11, an embodiment of a process chamber 200 for buoyant separation of a target constituent of a sample comprises: a frustoconical surface 210 defining a base region 220 having a first width and a collection region 230 having a second width, narrower than the first width, in opposition to the base region, wherein the frustoconical surface defines a volume 240 configured to receive the sample having the target constituent. In variations, the frustoconical surface can have a straight profile in elevation, as shown in FIGS. 3A and 3D. Alternatively, the frustoconical surface can have a curved profile or any other suitable profile in elevation, as shown in FIGS. 3B-3C. However, embodiments of the process chamber can be otherwise configured.

The volume 240 defined within the process chamber 200 preferably has a low height-to-width ratio, in order to facilitate rapid separation of the target constituent from the sample (e.g., by providing a smaller traveling distance for a given volume). However, the volume 240 defined within the process chamber 200 can alternatively have a high height-to-width ratio (e.g., as a slender volume, rectangle, cylinder), or any other suitable height-to-width ratio. However, the process chamber can be of any other suitable geometry.

The process chamber is preferably fabricated using glass or plastic materials, such as polystyrene, polypropylene, polycarbonate, cycloolefin, and/or glass. Furthermore, any surface (exterior and/or interior) of the process chamber can be optionally treated with a surface coating (e.g., to influence surface properties, adhesion properties, optical properties, etc.). However, the process chamber can be configured in any other suitable manner.

The process chamber 200 is preferably used to perform any combination of Block S110, Block S120, and/or Block S130, as described in Section 1, but can be used to perform any other suitable portion of the method 100. Embodiments, variations, and/or examples of the process chamber are further described in U.S. application Ser. No. 14/969,446, filed 15 Dec. 2015.

In variations, the process chamber 200 can be adapted from a commercially available (e.g., pre-manufactured) chamber, dish, vial, tube, well, microwell plate, or any other suitable container for handling volumes of fluids (e.g., as shown in FIG. 1D), but can alternatively be left unaltered. In examples, the process chamber is a 1.5 mL centrifuge tube, but can also be a 15 mL tube, 50 mL tube, or any other vessel configured to contain any other suitable volume. In other examples, the process chamber can be one of a plurality of process chambers within a multi-well plate (e.g., 96 well, 385 wells, 1536 wells, etc.) (e.g., as shown in FIG. 2D), enabling integration with automated sample handling systems and multiplexed sample processing in parallel (e.g., when the plates are stacked).

In an alternative variation of the process chamber, as shown in FIG. 1J, the process chamber can be a rectangular prism, or any other suitable geometry with a high aspect ratio, and configured to hold a large sample volume (e.g., 100 mL as opposed to 1.5 mL). To enhance separation towards the walls and then flotation to the top surface, each of the walls of the rectangular process chamber 500 are preferably configured at a 3° offset from vertical, but can be any other suitable angle (e.g., 1°, 5°, 10°, 15°, etc.). As shown in FIG. 1J, a specific example of the rectangular process chamber 500 has a broad face 510, a side face 530, and a bottom face 550, with a collection region 570 at the upper region of the process chamber 500. However, the process chamber 500 can include any number of faces with any suitable dimensions. A variation of the method utilizing the rectangular process chamber is described in Section 1 (Block S135). However, the rectangular process chamber can be in any other suitable manner to effectively promote an increase in complex-to-complex proximity metric for the set of target-bound complexes. Furthermore, the rectangular process chamber 500 can additionally include a solution addition unit 590 to allow for easy solution pouring into the rectangular process chamber. The solution addition unit 590 is preferably located at a corner of the upper surface of the process chamber opposing the bottom face 550, and proximal to the collection region 570, but can alternatively be positioned at any other suitable location to permit facile loading and/or extraction of fluid from the process chamber 500. Furthermore, the solution addition unit 590 can be configured to receive at least a portion of the target constituent extractor shown in FIGS. 21A-21B such that target-bound complexes can be transferred into a secondary container. Additionally and/or alternatively, the solution addition unit 590 can be configured to fluidically seal solution addition unit 590 from the bottom face 550 by twisting the solution addition unit 590, completely removing solution addition unit 590 from the process chamber, adding a valve between the bottom face 550 and the solution addition unit 590, and/or can be otherwise configured with any other suitable subelement of the system.

The process chamber 200 can be optionally modified to increase the aggregation of target-bound complexes at a specific location of the process chamber (e.g., the interior sidewall 210 of the process chamber) to enhance isolation. In one variation, the process chamber 200 can encourage localization of target-bound complexes with at least one set of chamber morphologies (e.g., ridges, protrusions, grooves, etc.) that are preferably fabricated using the press-fit process, but can be fabricated using any other suitable manufacturing technique, (e.g., micromachining, photolithography, 3D-printing, injection molding, laser-etching, roughening, scoring, tapping/threading, etc.). Furthermore, the set of chamber morphologies can be adhered to the surface of the sidewall using any suitable method (e.g., lamination, heat-bonding, laser-bonding, anodic bonding), or otherwise joined to the sidewall. In a second variation, the interior surfaces can be treated with surface coatings (e.g., dip-coating, spray-coating, micropatterning, etc.), including chemical coatings, polymer coatings, and/or optical coatings. However, the interior sidewall 210 can include a single feature, or any other suitable number of features within the set of chamber morphologies configured to enable retention, or localization of a population of target-bound complexes within the process chamber at a collection region 230.

In one variation, as shown in FIG. 20A and FIG. 20B, the sidewall 210 of the process chamber 200 is patterned through a press fit process and includes a set of protrusion features 235 (e.g., blocks, bumps, protrusions, positive space, etc.) that extend into the interior volume of the process chamber. The set of protrusion features 235 can be fabricated from any suitable material (e.g., polymer, metal, etc.). The set of protrusion features preferably includes features with homogenous shape, dimension, and spacing, but can additionally and/or alternatively include features with varying morphology, distribution, and/or any suitable combination thereof. In a first example, as shown in FIG. 20A, the process chamber includes a set of triangular ridges 235, wherein each ridge has a ridge depth 236 (e.g., orthogonal to the side wall) and a between-ridge spacing 237 (e.g., along the sidewall), defined between adjacent ridges of the sidewall 210. Each ridge in the set of ridges is the same dimension and spacing. In operation, as fluid is removed from the process chamber, target-bound complexes can settle into the between-ridge spacing 237, thus enabling non-target constituents to be fully removed from the process chamber 200. To enhance the attraction of target-bound complexes to the sidewall 210 in aqueous systems, the ideal ratio of ridge depth 236 to between-ridge spacing 237 is within the range of 5:1 to 1:50. In another variation of the first example, as shown in FIG. 20B, the ridge depth 236 and ridge diagonal surface 238 can be patterned in a step-like manner, where the ratio of the ridge depth 236 to diagonal surface 238 can include ratios of (1:1, 1:10, 1:100, 1:1000, and 1:10000). In a second example, the between-ridge spacing can decrease with corresponding height of the ridge on the sidewall, forming a patterned gradient of triangular ridges along the longitudinal axis of the sidewall, wherein the density of triangular ridges increases near the upper region of the process chamber. Preferably, the set of protrusion features 235 is continuous around the entirety of a specific height of the process chamber 200, but can alternatively be fabricated on a subregion of the sidewall 210. However, the protrusion features 235 of the sidewall 210 can be otherwise configured, and can additionally and/or alternatively be used in combination with recessed features 245.

Figure 20C:
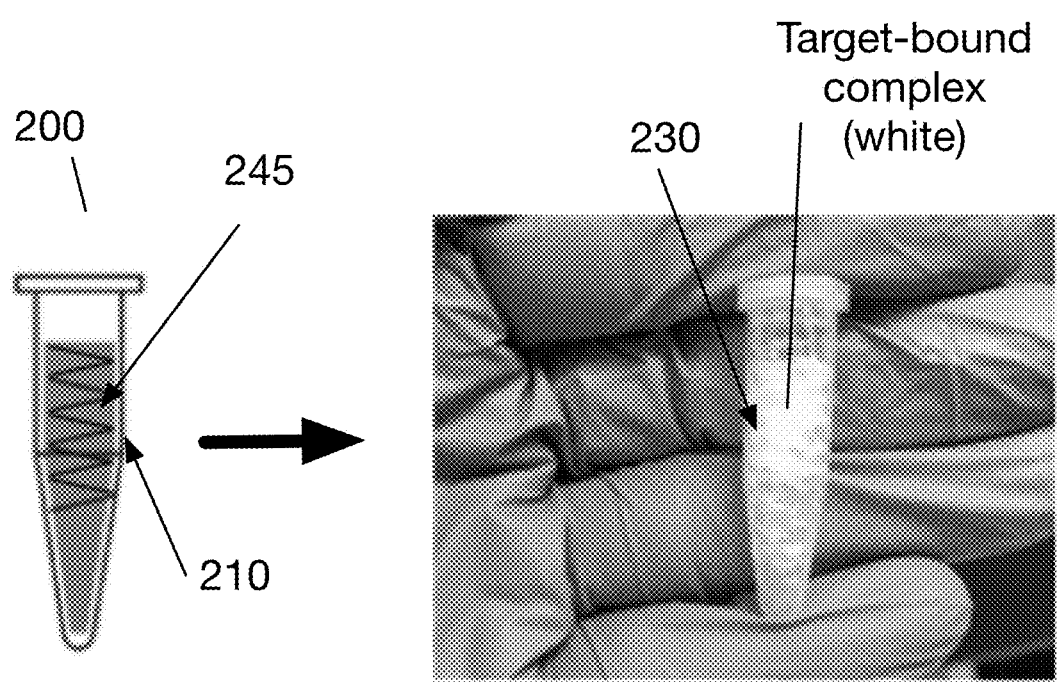
FIG. 20C depicts a variation of a subcomponent of a process chamber used in an embodiment of a system for buoyant separation of a target constituent of a sample.

In a second variation, the sidewall 210 of the process chamber 200 is patterned through a press fit process and includes a set of recessed features 245 (e.g., holes, grooves, slots, negative space, etc.). The set of recessed features 245 can include features of homogenous shape, dimension, and spacing, but can additionally and/or alternatively include features with varying morphology, distribution, and/or any suitable combination thereof. In an example, as shown in FIG. 20C, the sidewall 210 of the process chamber 200 can be texturized through a scoring process (e.g., manually or automated using a sharp edge, needle, etc.). The texture of the sidewall can include any suitable combination of patterns, depth, width, or feature, such that the target-bound complexes have affinity for the lateral portions of the sidewall (e.g., collection region 230) as fluid is removed from the vial. In a second example, as shown in FIG. 1i, the sidewall includes a single recessed feature 250, configured to retain a population of target-bound complexes at the collection region 230 (e.g., upper region of the process chamber). In a third example, the sidewalls of a 1.5 mL centrifuge tube can be tapped, wherein a set of internal threads along the sidewall of the centrifuge tube can be formed using an M9-sized tap or any other suitable tool (e.g., spiral flute tap, spiral point tap, pin, plug, etc.). The modified (e.g., threaded) sidewalls of the centrifuge tube can then be used to efficiently capture target-bound complexes around the entire circumference and upper section of the tube (e.g., due to surface tension between the sample fluid and the set of internal threads of the sidewall), However, the process chamber can be otherwise modified and/or configured. Preferably, the set of recessed features 245 is continuous around the entirety of a specific height of the process chamber 200, but can alternatively be fabricated on a subregion of the sidewall 210. However, the recessed features 245 of the sidewall 210 can be otherwise configured, and can additionally and/or alternatively be used in combination with protrusion features 235.

Alternatively, in a third variation, the sidewall of the process chamber includes features configured to move target-bound complexes away from (e.g., rather than towards) the sidewall (e.g., increasing the flow velocity of the buoyant particles to a collection region). In one example, as shown in FIG. 1J, each of the sidewalls of a rectangular process chamber are fabricated at a set angle offset from vertical (e.g., 3° offset), enabling concentration of the buoyant particles in separation steps described in Section 1. However, the sidewalls of the process chamber can be configured in any other suitable manner to manipulate the movement and location of target-bound complexes.

Figure 9A:
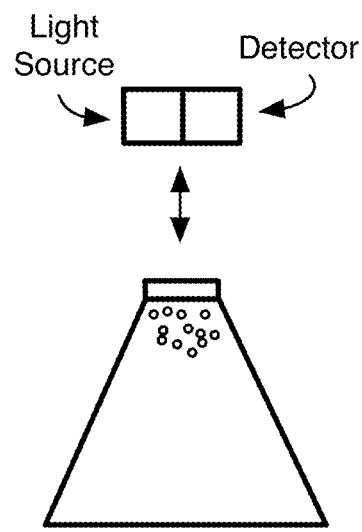
FIGS. 9A-9B depict variations of a process chamber comprising a detection window in an embodiment of a method for buoyant separation of a target constituent of a sample.
Figure 9B:
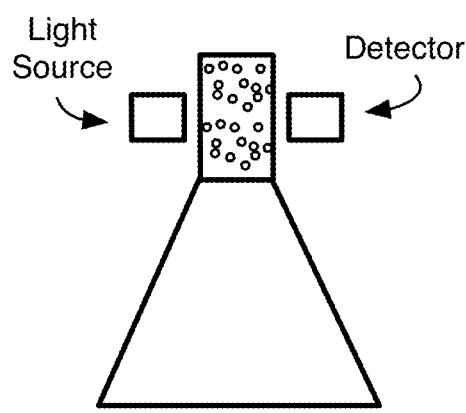

Additionally or alternatively, in some variations, the process chamber 200 can include a window 260 configured adjacent to the collection region 230, wherein the window comprises a planar substrate configured to enable observation of target-bound complexes aggregated at the collection region, as shown in FIG. 9A, or alternatively defines a detection volume configured to receive the population of target-bound complexes from the collection region and to interface with a detector module, as shown in FIG. 9B.

Additionally or alternatively, in some variations, the process chamber can comprise or be coupled to a dip tube 270 comprising a first end that couples to a fluid transfer element (e.g., a pipette tip) and a second end configured inferior to the collection region at which buoyant substrates aggregate, in order to enable fluid transfer in the process chamber substantially without disturbance of the buoyant substrates. In examples, the dip tube can be incorporated into a lid of the process chamber, as shown in FIG. 12A, incorporated into a wall of the process chamber, as shown in FIG. 12B, be a modular component that interfaces with the process chamber (e.g., by adhering to a wall of the process chamber with a membrane), and/or cooperate with the process chamber in any other suitable manner.

Additionally or alternatively, in some variations, the process chamber 200 can comprise a cap 280 in communication with the collection region, wherein the cap 280 facilitates extraction of the population of target-bound complexes from the collection region of the process chamber. An additional example of a portion of the process chamber is shown in FIG. 13.

In related embodiments of a system 300 for separating and extracting a population of target-bound complexes from a sample, embodiments and variations of which are shown in FIGS. 14-17C, the system 300 can include a process chamber 310 and an extraction apparatus 350 configured to interface with the sample containing chamber 310 in different operation modes, in order to facilitate separation and/or enable extraction of a population of target-bound complexes from the sample. Alternative variations of these embodiments of the system 300 can, however, omit the process chamber 310.

In the related embodiments of the system 300, the process chamber 310 functions to hold a sample and can additionally or alternatively function to facilitate mixing of the target constituent of the sample with a volume of buoyant substrates to produce a population of target-bound complexes. The process chamber 310 preferably has a closed end and an openable end (e.g., an end configured to be opened, a permanently open end, etc.) opposing the closed end, the process chamber configured to hold the sample having the target constituent and facilitate binding of the target constituent to a set of substrates to produce a set of buoyant target-bound complexes. The process chamber 310 is preferably substantially rigid; however, the process chamber can alternatively be deformable (e.g., under compression, under tension, under torsion, etc.). In a specific example, the process chamber 310 is composed of plastic; however, the process chamber 310 can alternatively include regions composed of one or more of: a ceramic material, a metallic material (e.g., to aid magnetic separation), and any other suitable material. Furthermore, the process chamber 310 can additionally or alternatively be configured in any other suitable manner.

2.2 System—Extraction Apparatus

In the related embodiments of the system 300, the extraction apparatus 350 (i.e., target constituent extractor) functions to provide a surface or volume at which or into which the population of target-bound complexes can be transmitted, thereby facilitating extraction of the population of target-bound complexes from a bulk volume of the sample. In the related embodiments, the extraction apparatus can comprise elements and/or be configured in any other suitable manner (e.g., with surface treatments, protrusion features, recessed features) that enable retention of the population of target-bound complexes at the extraction apparatus 350, such as those described in the above Section 2.1. The extraction apparatus 350 is preferably used to perform Block S140 described in Section 1, but can be used to perform any other suitable portion of the method 100. Embodiments, variations, and/or examples of the extraction apparatus are further described in U.S. application Ser. No. 14/969,446, filed 15 Dec. 2015.

In a first variation, as shown in FIGS. 15A-15D and, the system 300' includes a sample containing chamber 310' defining a volume for retention of the sample, within which the target constituent(s) of the sample can be combined with a volume of buoyant substrates that enable isolation of the target constituent from the sample in the form of a population of target-bound complexes. In the first variation, the extraction apparatus 350' comprises a first portion 360' including a frustoconical surface 362' that defines a feeding region 363' into an opening 364' (e.g., having an inverted frustoconical surface that opposes the frustoconical surface 362') at a superior portion of the first portion 360'; and a second portion 370' comprising a collection tube 372' that interacts with the opening 364' of the feeding region 363' to receive particles of the population of target-bound complexes from the sample. In the first variation, the frustoconical surface defines a base region that interfaces with the sample volume in the process chamber 310', and a concentration region (associated with the opening 364') above and in opposition to the base region, wherein the frustoconical surface defines a volume configured to concentrate the set of buoyant target-bound complexes at the concentration region of the frustoconical surface. Furthermore, in the first variation, the extraction apparatus 350' can include a separation zone having an inverted frustoconical surface 366', in communication with the concentration region of the frustoconical surface 362' by a channel 365' that transmits the set of buoyant target-bound complexes into the separation zone, for removal of the set of buoyant target-bound complexes from the concentration region. In the first variation, the second portion 370' of the extraction apparatus 360' can include a venting chamber 374' configured to provide venting of the sample containing chamber 310' during relative displacement between the sample containing chamber and the extraction apparatus 350' for extraction of the population of target-bound complexes from the sample.

Figure 15B:
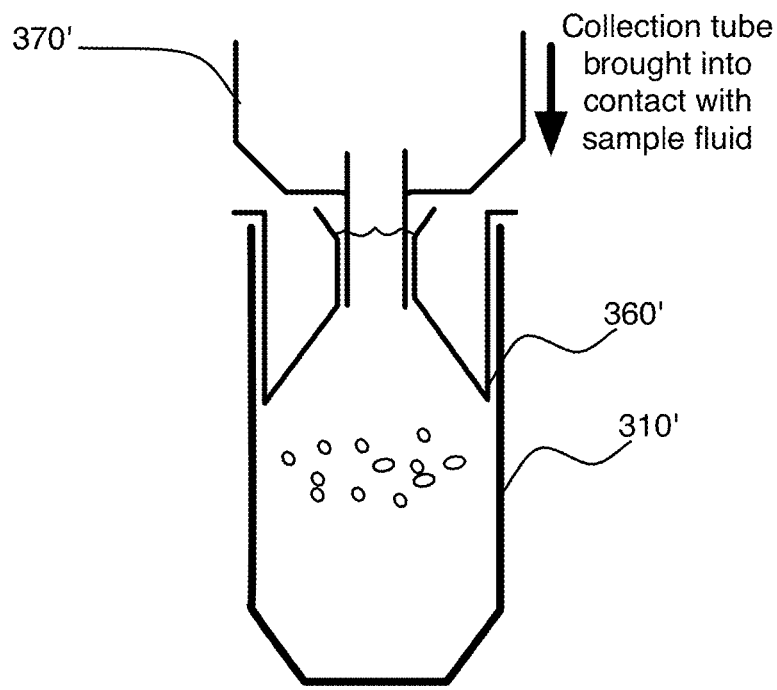
Figure 15C:
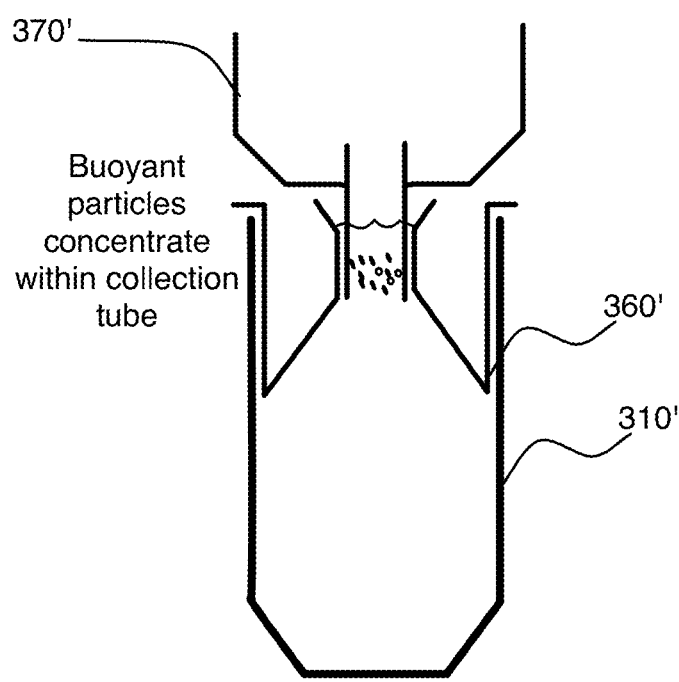
Figure 15D:
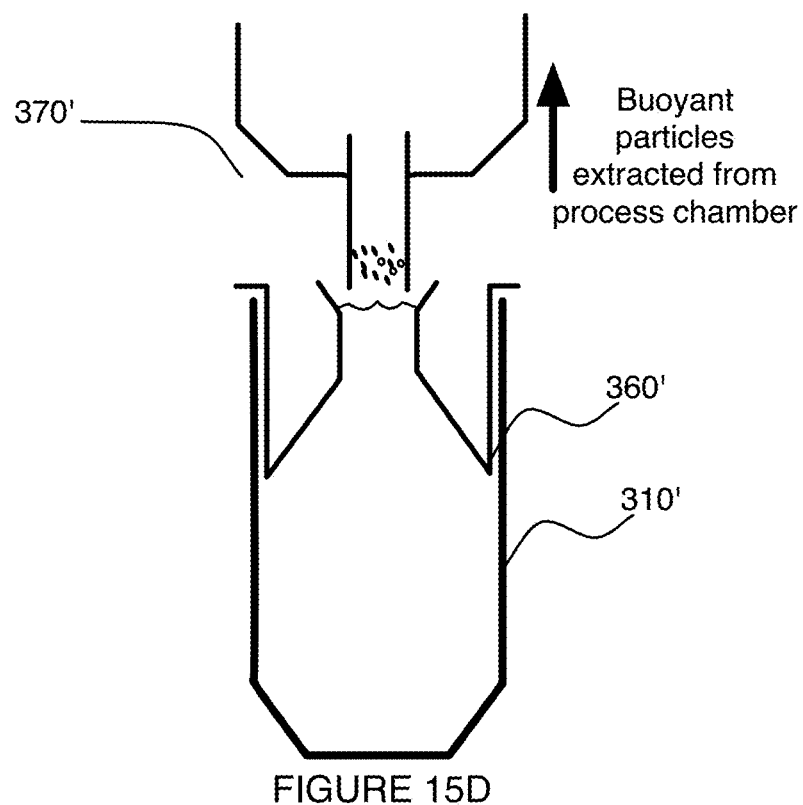
Figure 15E:
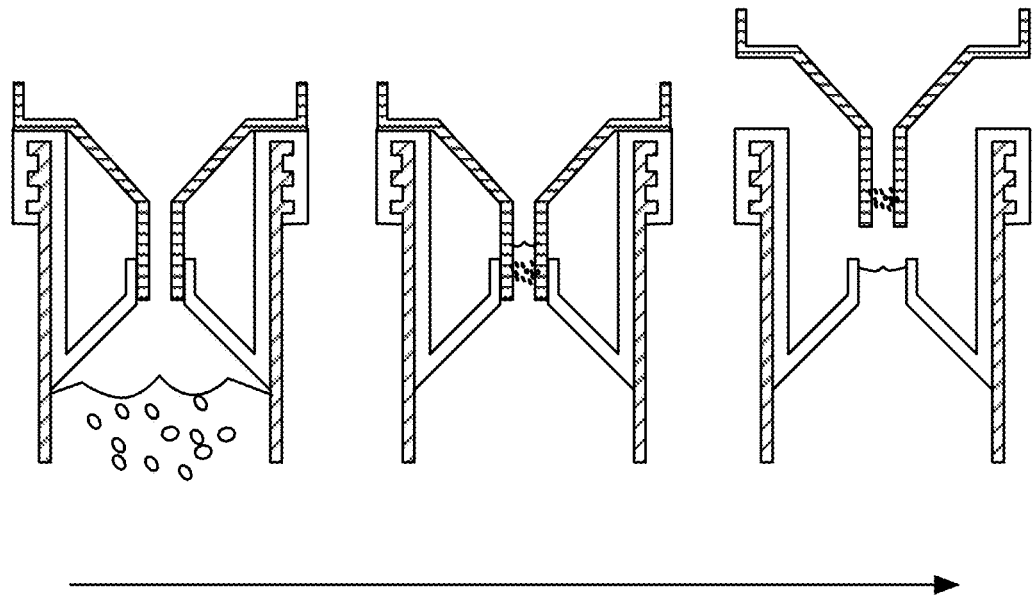
FIG. 15E depicts an example related to the first variation of an embodiment of a system for buoyant separation of a target constituent of a sample.
Figures 16A, 16B:
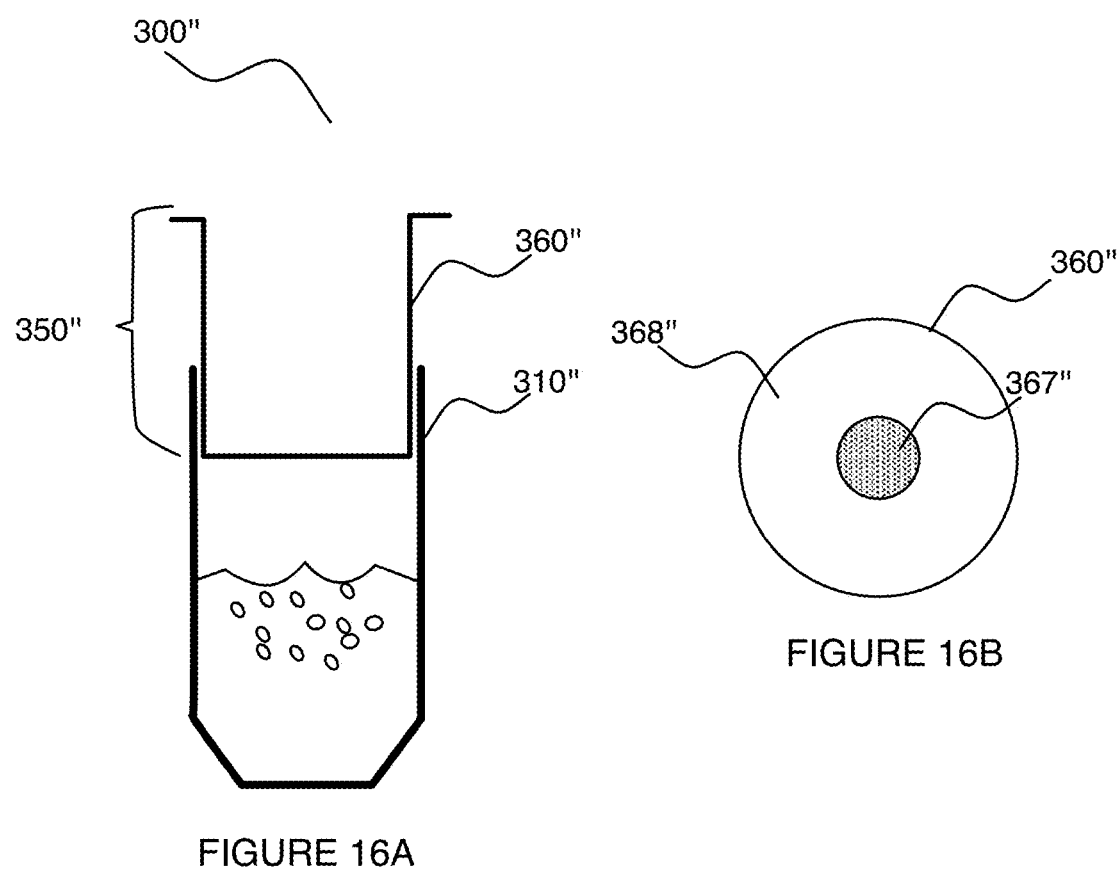

In the first variation, the first portion 360' of the extraction apparatus 350' having the frustoconical surface 362' preferably interfaces with a surface of the sample fluid in a first configuration (e.g., a compressed configuration), as shown in FIG. 15B, such that the feeding region 363' receives fluid of the sample and enables feeding of the population of target-bound complexes toward the opening 364' due to buoyant separation. In the first configuration, the collection tube 372' is in position to receive the population of target-bound complexes as they float in an inferior-to-superior direction, as shown in FIG. 15C. Finally, uncoupling of the second portion 370' from the first portion 360' of the extraction apparatus 350', as shown in FIG. 15D, enables extraction of the population of target-bound complexes from the sample, by way of the collection tube 372' of the second portion 370' of the extraction apparatus 350'. In the first variation, the first portion 360' and the second portion 370' of the extraction apparatus 350' can be positioned together and/or separately with respect to the process chamber 310' of the process chamber 300'. Furthermore, in the first variation, the first portion 360' and the second portion 370' of the extraction apparatus 350' can be displaced relative to each other and/or relative to the process chamber 310' by any one or more of a: screw mechanism, a sliding mechanism, a ratcheting mechanism, a magnetic mechanism, and any other suitable mechanism. Furthermore, motion between components of the system 300' of the first variation can be limited to a specified range (e.g., with a tab), in association with phases of sample processing to extract the target constituent from the sample.

In variations of the first variation, the opening 364' of the feeding region 363' and the collection tube 372' preferably mate with each other in a complementary manner, and furthermore are flush with each other in order to provide a sufficient seal that prevents particles of the population of target-bound complexes from entering undesired portions of the process chamber 300'. As such, in a specific example where the feeding region 363' is associated with the inverted frustoconical surface 366', as shown in FIG. 15A, the collection tube 372' can be coupled to a second inverted frustoconical surface 376' that is complementary to the inverted frustoconical surface 366' coupled to the feeding region 363'. However, the first portion 360' and the second portion 370' can alternatively interact with each other in any other suitable manner. Additionally or alternatively, in variations of the first variation, the process chamber 310' can receive fluid (e.g., buffer, sample) through a port (e.g., within the process chamber 310' and/or the extraction apparatus 350', in order to facilitate delivery of the population of target-bound complexes toward the feeding region 363' and/or the collection tube 372'.

In another variation of the first variation, as shown in FIGS. 21A and 21B, the extraction apparatus 350' comprises a first portion 360' including a single frustoconical surface 362' that defines a feeding region 363' into an opening 364' that forms a continuous fluidic pathway to the collection tube 372', such that the buoyant particles can pass from the sample containing chamber 380 to an upper chamber 385. Upon relocation of the target-bound complexes to the upper chamber 385, the upper chamber 385 (e.g., a separate collection tube, secondary container) can be closed and removed from the sample containing chamber 380 (e.g., a process chamber), such that fluid in the upper chamber 385 can be manipulated without any fluidic contact with the sample containing chamber 380. In one example, as shown in FIG. 21B, the first portion 360' can be configured as a collection plunger that operates in coordination with a valve slit 390 coupled to a vent path 392, and can optionally include a seal 395 that allows coupling of the extraction apparatus 350' to the sample containing chamber 380. When the upper chamber 385 is coupled to the sample containing chamber 380, the collection plunger can be arranged in a first configuration (e.g., lowered configuration) to enable target-bound complexes to travel into the upper chamber 385, wherein the valve slit 390 is closed and air is unable to pass through the vent path 392. Once transfer is complete, the upper chamber 385 can be secured with the separator lid 398 and removed from the sample containing chamber 380, thus opening the vent path 392 to allow air to pass through the valve slit such that the fluid in the upper chamber 385 stays in the upper chamber 395. In one variation, upon removal of the upper chamber from the process chamber, the upper chamber can be fluidly sealed using a vertically-aligned plug (e.g., valve, pin, etc.) inserted at the base of the upper chamber, thus allowing the separator lid to be removed from the top surface of the upper chamber for enriched sample processing. However, the extraction apparatus 350' can be otherwise secured and or/configured to enable manipulation and downstream processing of the enriched sample contained in the upper chamber after extraction.

In an alternative variation of the first variation, the extraction apparatus 350' can omit a second portion 370', where buoyant particles are configured to be transmitted from the process chamber 310' into the inverted frustoconical surface 366' of the first portion 360' (according to one or more of the methods describe in Block S140 above), and extracted from the inverted frustoconical surface 366' (according to methods described above).

Furthermore, while frustoconical surfaces are described in relation to the extraction apparatuses 350, 350', variations of the extraction apparatus can alternatively define any other suitable surface (e.g., broadening surface, narrowing surface) configured to facilitate concentration and/or extraction of buoyant particles from the process chamber.

In a second variation, as shown in FIGS. 16A-16F, the system 300" includes a process chamber 310" defining a volume for retention of the sample, within which the target constituent(s) of the sample can be combined with a volume of buoyant substrates that enable isolation of the target constituent from the sample in the form of a population of target-bound complexes. In the second variation, the extraction apparatus 350' comprises a first portion 360" including a hydrophilic region 367" and a hydrophobic region 368" at a surface configured to interface with a surface of sample fluid within the sample containing chamber 310". In the second variation, the hydrophilic region 367" is surrounded by the hydrophobic region 368", in order to define an area at which the population of target-bound complexes can be retained for extraction from the sample containing chamber 310". The size of the hydrophilic region 367" in the second variation can further be adjusted or adjustable to provide an area sufficient in size to retain a desired portion of the population of target-bound complexes at the first portion 360" of the extraction apparatus 350". In the second variation, the hydrophilic region 367" can be located at an external surface of the first portion 360" that interfaces with fluid of the sample in the sample containing chamber 310", or can alternatively be located at an interior surface of the first portion 360", and accessible through an opening into the first portion 360" that also enables venting of the process chamber during extraction. Additionally or alternatively, the hydrophilic region 367" can be composed of the same material as the first portion 360" of the extraction apparatus 350", wherein a coating of hydrophobic material provides the hydrophobic region 368" and isolates the hydrophilic region 367" to a desired area of the extraction apparatus. Furthermore, the hydrophilic region 367" can comprise any suitable morphology (e.g., convex morphology, textured morphology) that enhances contact between the hydrophilic region 367" and fluid of the sample in the sample-containing chamber 310".

In the second variation, the first portion 360" of the extraction apparatus 350" preferably interfaces with a surface of the sample fluid in a first operation mode (e.g., a compressed configuration), as shown in FIG. 16D such that the hydrophilic region 367" interfaces with the population of target-bound complexes due to buoyant separation in the sample. Upon displacement of the first portion 360" of the extraction apparatus 350" away from the sample container 310" in a second operation mode, as shown in FIG. 16E, the population of target-bound complexes, coupled to the hydrophilic region 367" by adhesion forces, is extracted from the sample containing portion 310" of the process chamber 300". Finally, uncoupling of the first portion 360" from the process chamber 310"', as shown in FIG. 16F, enables extraction of the population of target-bound complexes from the sample. In the second variation, the population of target-bound complexes can then be retrieved (e.g., by pipetting) from the hydrophilic region 367" of the first portion 360" of the extraction apparatus. Similar to the first variation of the process chamber 300', in the second variation, the first portion 360" of the extraction apparatus 350' can be displaced relative to the sample containing chamber 310" by any one or more of: a screw mechanism, a sliding mechanism, a ratcheting mechanism, a magnetic mechanism, and any other suitable mechanism. Furthermore, motion between components of the process chamber 300' of the first variation can be limited to a specified range (e.g., with a tab), in association with phases of sample processing to extract the target constituent from the sample.

Figure 17A:
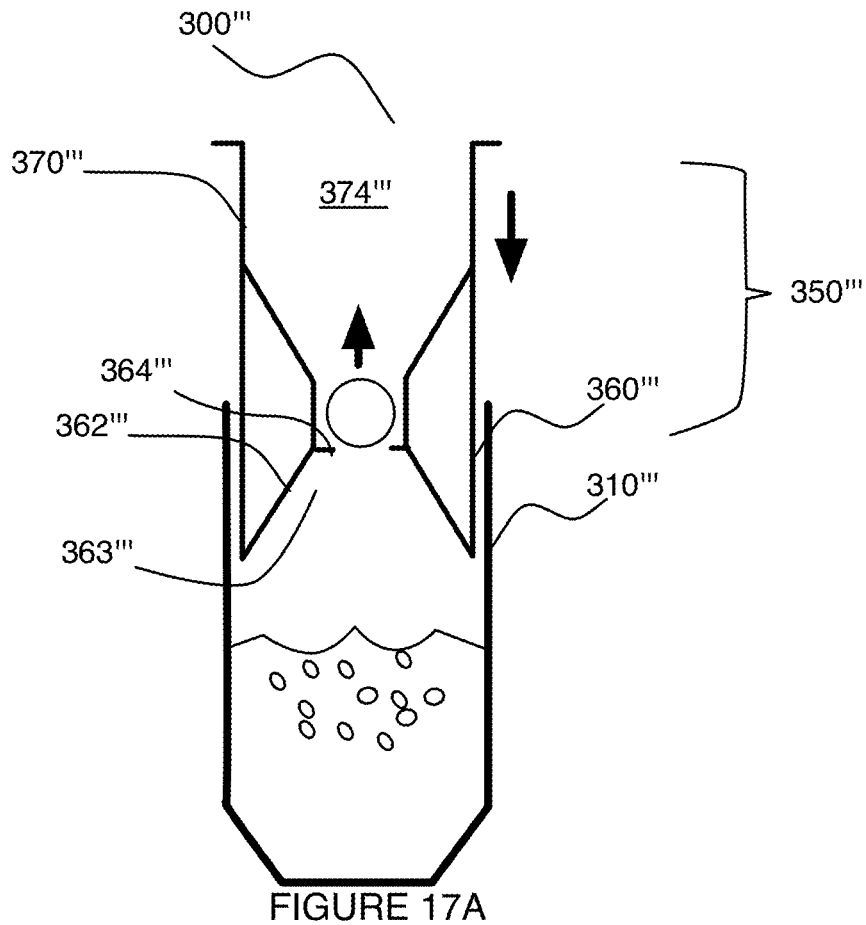
FIGS. 17A-17C depict a variation of an embodiment of a system for buoyant separation of a target constituent of a sample.
Figure 17B:
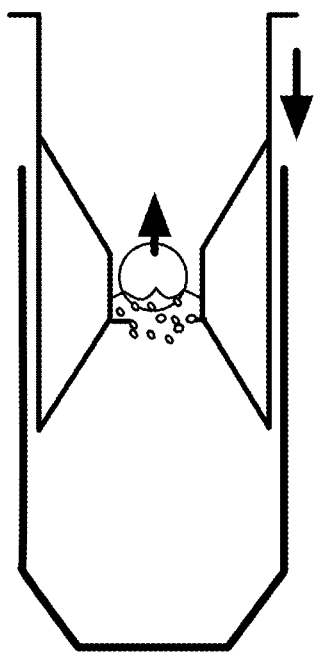
Figure 17C:
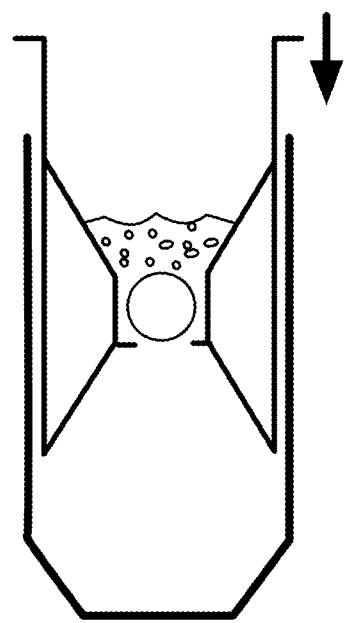

In a third variation, as shown in FIGS. 17A-17C the process chamber 300"' includes a sample containing chamber 310"' defining a volume for retention of the sample, within which the target constituent(s) of the sample can be combined with a volume of buoyant substrates that enable isolation of the target constituent from the sample in the form of a population of target-bound complexes. In the first variation, the extraction apparatus 350"' comprises a first portion 360"' including a frustoconical surface 362"' that defines a feeding region 363"' into an opening 364"' at a superior portion of the first portion 360"'; and a second portion 370"' comprising a valve 376"' (e.g., a ball valve, other valve, etc.) that interfaces with the opening 364"' in permitting controlled passage of the population of target-bound complexes into a collection region 378"' of the second portion 370"'. In the third variation, the second portion 370"" includes a venting chamber 374"" having an inverted frustoconical surface opposing the frustoconical surface 362"', configured to provide venting of the sample containing chamber 310"" during relative displacement between the sample containing chamber and the extraction apparatus 350"" for extraction of the population of target-bound complexes from the sample.

In the third variation, the first portion 360"" of the extraction apparatus 350"' preferably interfaces with a surface of the sample fluid in a first configuration (e.g., a compressed configuration, prior to addition of fluid into the venting chamber 374"', etc.), as shown in FIG. 17B, such that the feeding region 363"' receives fluid of the sample and enables feeding of the population of target-bound complexes toward the opening 364"' due to buoyant separation. In the first configuration, the valve 376"' is displaced by fluid of the sample at a superior region of the process chamber 310"', thus allowing passage of the population of target-bound complexes, through the opening 364"' and into the venting chamber 374"' of the second portion 370"' of the extraction apparatus 350"', as shown in FIG. 17C. Finally, uncoupling of the extraction apparatus 350"' from the sample containing chamber 310''' enables extraction of the population of target-bound complexes from the sample. In the third variation, a specific volume of fluid (e.g., 100 μL, 200 μL) can be configured to pass into the second portion 370''' of the extraction apparatus 350''' upon transmission of the extraction apparatus 350''' into the first configuration within the process chamber (e.g., by linear displacement, by screwing the extraction apparatus and the process chamber relative to each other, etc.). The specific volume of fluid can be limited by a physical feature (e.g., notch) of the process chamber 300''' that physically stops fluid passage past the valve 376''' once the set volume of fluid has been obtained. However, the specific volume of fluid can be limited in any other suitable manner.

Similar to the first variation of the system 300, in the third variation, the first portion 360''' and the second portion 370''' of the extraction apparatus 350''' can be displaced relative to the sample containing chamber 310''' by any one or more of a: screw mechanism, a sliding mechanism, a ratcheting mechanism, a magnetic mechanism, and any other suitable mechanism. Furthermore, motion between components of the system 300''' of the first variation can be limited to a specified range (e.g., with a tab), in association with phases of sample processing to extract the target constituent from the sample. The system 300 can, however, comprise any suitable combination of the above variations and/or any other suitable process chamber for processing a sample and enabling extraction of a target constituent from the sample.

Additionally and/or alternatively, variations of the process chamber and or/the extraction apparatus 350, 350' can be integrated into an automated system for removal and manipulation of sample volumes. Furthermore, modification of the sidewalls of any portion of the extraction apparatus (e.g., process chamber 310, first portion 360, collection tube 372, second portion 370, etc.) can allow target-bound complexes to be transferred in a predictable manner, such that automated system can reliably extract fluid target-bound complexes and/or surrounding fluid. In one variation, using microbubbles substrate particles in a microwell plate (e.g., 96 to 1536 well plates), separation of target-bound complexes from the total sample volume can be performed across multiple plates simultaneously and in parallel, as opposed to in series (as is done with magnetic particle manipulation), increasing throughput and minimizing the number of steps for separation. In one example, parallel processing (e.g., separation and extraction of target-bound complexes from multiple samples simultaneously) can be achieved using an automated system by stacking microwell plates. Once target-bound complexes have been transferred to the upper portion of the microwells (e.g., by flotation, at a specific time after combination), multiple plates can be simultaneously (e.g., via automation) re-positioned for targeted removal of substrate-bound complexes proximal the upper surface of the sample fluid (e.g., at the meniscus), and/or the non-target fluid (e.g., supernatant) proximal the lower surface of the sample fluid (e.g., below the meniscus). However, automation of separation and extraction steps can be performed using any suitable combination of subcomponents of the system, in any other suitable manner.

As such, the process chamber systems 200, 300 are preferably configured to perform at least a portion of the method 100 described in Section 1 above; however, the process chamber 200 can additionally or alternatively be configured to perform any other suitable method.

2.3 System—Alternative Variations

Figure 18A:
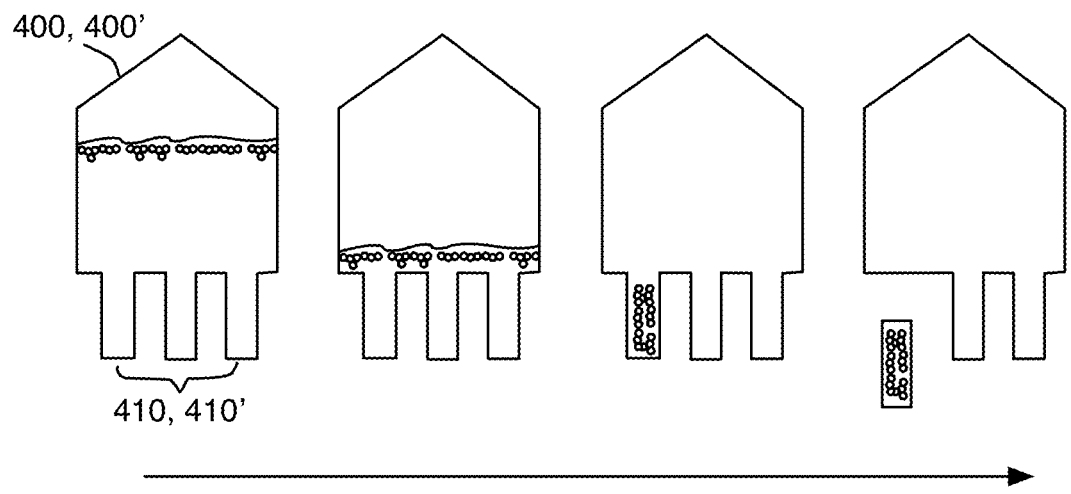
FIGS. 18A-18B depict an alternative embodiment of a system for buoyant separation of a target constituent of a sample.
Figure 18B:
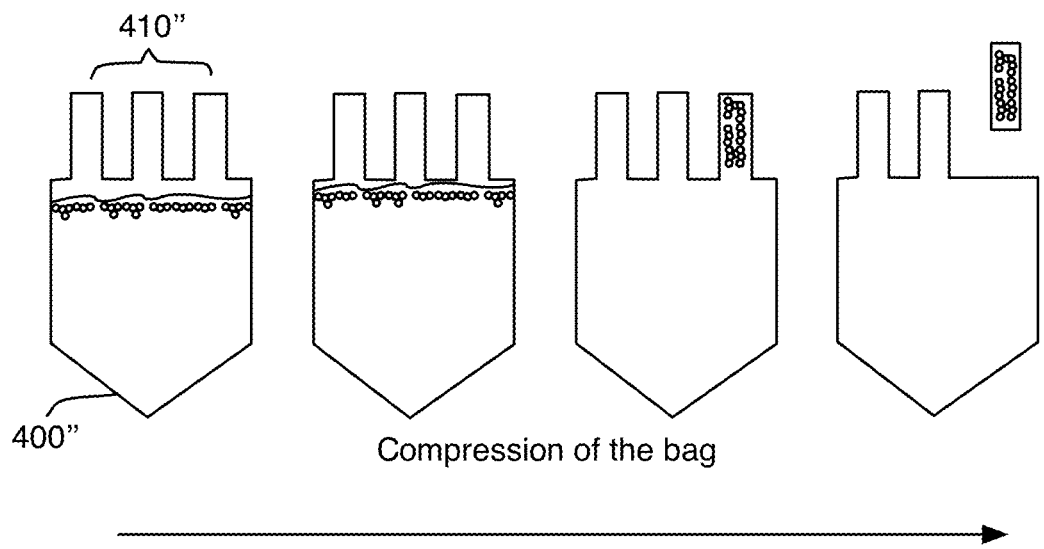

Alternative variations of the process chambers 200, 300 can, however, comprise any other suitable container (e.g., fluid receiving and/or distributing bag). For instance, in one variation aspects of the separation and/or extraction elements of the systems described above can be incorporated into a bag-type form factor (e.g., blood transfusion bag, leukopheresis bag, cell collection bag, etc.), where generating a population of target-bound complexes is performed, and the bag-type form factor facilitates separation and/or extraction of the population of target-bound complexes from a sample volume. Furthermore, bag-type form factors can be used in closed-system operation, allowing higher sterility for sensitive samples. In one such variation, as shown in FIGS. 18A and 18B, the bag 400 can include a set of stems 410 incorporated into the bag, that function to enable accessing of the bag for filling and emptying of contents of the bag 400. The stems 410 can additionally or alternatively function to facilitate testing of a sample (e.g., blood type cross-matching, creation of a closed system for sterile extraction, sample enrichment, cell signaling, etc.). In operation, the set of stems 410 can thus allow buoyant particles to be received into the bag 400, to interact with and bind to sample constituents of interest, and then to be separated, for instance, using a sealing mechanism (e.g., heat sealing mechanism) to seal portions of the bag 400 containing the buoyant particles from portions of the bag 400 that are substantially void of the buoyant particles.

In a first variation, as shown in FIG. 18A, the bag 400' can include a set of inferiorly located stems 410', such that draining of the bag 400' through one or more of the stems 410' causes a population of target-bound complexes within the bag to enter the stems 410', with a small amount of sample fluid, for extraction. Additionally or alternatively, in the first variation, one or more stems 410' of the bag 400' can be sealed off and/or removed from the bag 400', thereby enabling extraction of the population of target-bound complexes from the bulk sample.

In a second variation, as shown in FIG. 18B, the bag 400" can include a set of superiorly located stems 410", such that delivery of the population of target-bound complexes into the stems 410" (e.g., through compression of the bag, through buoyant forces, etc.) allows the population of target-bound complexes to be separated from the bulk sample volume in the bag 400". Additionally or alternatively, in the second variation, one or more stems 410" of the bag 400' can be sealed off and/or removed from the bag 400", thereby enabling extraction of the population of target-bound complexes from the bulk sample.

In still alternative embodiments, a process chamber 600, as shown in FIG. 19A, can include an outlet 610, wherein the outlet 610 can include one or more of: a puncturable diaphragm, a luer lock, a valve, and/or any other suitable outlet. The outlet can thus allow sample fluid and/or non-buoyant particles to be removed from the process chamber 600, without disturbing a region of separated buoyant particles. In variations of these alternative embodiments, the outlet 610 can thus facilitate one or more of: negative separation (e.g., to remove non-target constituents from the sample) and positive separation (e.g., to remove target constituents from the sample). Additionally or alternatively, the process chamber 600 and/or outlet 610 can facilitate performance of chemistry on buoyant particles (e.g., in a two-phase solvent system). Additionally or alternatively, the process chamber 600 and/or outlet 610 can facilitate removal of compromised buoyant particles (e.g., broken buoyant particles) from the bulk sample volume. However, the chamber 600 and/or outlet 610 can facilitate any other suitable operation in relation to the population of target-bound complexes.

In one variation, the process chamber 600' can include an inferiorly located outlet 610', such that draining of the process chamber 600' through the outlet 610' causes a population of target-bound complexes within the process chamber 600' to enter an inferior region of the process chamber 600' (in the orientation shown in FIG. 19B), with a small amount of sample fluid, for extraction. Additionally or alternatively, in the first variation, the inferior region 620' of the process chamber 600' can be configured to separate from the remainder of the process chamber 600', as shown in FIG. 19B, thereby enabling extraction of the population of target-bound complexes from the bulk sample.

In an alternative variation, as shown in FIG. 19C, the process chamber 600" can include a superiorly located outlet 610", wherein delivery of the population of target-bound complexes into a superior region 620" of the process chamber 600' (e.g., through buoyant forces, etc.) allows the population of target-bound complexes to be separated from the bulk sample volume in the process chamber 600". Additionally or alternatively, in the second variation, the superior region 620" of the process chamber 600" can be sealed off and/or removed from the remainder of the process chamber 600", thereby enabling extraction of the population of target-bound complexes from the bulk sample. Additionally or alternatively, the process chamber 600" of this variation can be inverted, non-buoyant components of the sample can be drained from outlet 610", and then the process chamber 600" can then be reverted to a non-inverted orientation, whereby the population of target-bound complexes remains in the superior region 620" of the process chamber 600" due to surface tension between fluid coupled to the population of target-bound complexes and the wall of the superior region 620" of the process chamber. The superior region 620" of the process chamber 600" can then be sealed off and/or removed from the remainder of the process chamber 600", thereby enabling extraction of the population of target-bound complexes from the bulk sample.

Additionally or alternatively, variations of the process chambers 200, 300 can be composed of or otherwise include metallic regions (e.g., magnetic regions, ferromagnetic regions) configured to facilitate magnetic separation of the target constituent(s) of the sample according to methods described in Section 1 above. For instance, magnetic/ferromagnetic regions can facilitate formation of stray fields and/or directed magnetic fields that enable magnetic separation of sample components in addition to or in alternative to buoyancy-based separation methods.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The method 100 and/or system 200 of the preferred embodiment can be embodied and/or implemented at least in part as machine configured to receive a computer-readable medium storing computer-readable instructions. The instructions are preferably executed by computer-executable components preferably integrated with the system and one or more portions of the processor and/or analysis engine. The computer-readable medium can be stored in the cloud and/or on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

We claim:

1. A system for facilitating the separation of a set of target materials from a sample, the system comprising:
    a set of buoyant spheres, the set of buoyant spheres associated with a first density;
    a container comprising a deformable bag, the deformable bag configured to be separable into a set of multiple portions;
    an automated fluid handling subsystem, wherein the automated fluid handling subsystem is configured to:
        add, to the deformable bag, the sample associated with a second density, the second density greater than the first density, wherein the sample comprises:
            the set of target materials;
            a set of non-target materials;
        add, to the deformable bag, the set of buoyant spheres, wherein the set of buoyant spheres is configured to bind with at least a portion of the set of target materials, thereby producing a set of target-bound materials;
        with a sealing component, separate the deformable bag into the set of multiple portions, thereby enabling accumulation of the set of target-bound materials at a predetermined region of an internal volume of the deformable bag, thereby facilitating the separation.

2. The system of claim 1, wherein the predetermined region is a superiorly-located portion of the set of multiple portions.

3. The system of claim 1, wherein the deformable bag further comprises a draining component, wherein the draining component is configured to enable a draining process of non-target materials from the deformable bag.

4. The system of claim 3, wherein the draining process is configured to be implemented after separation of the deformable bag into the set of multiple portions.

5. The system of claim 4, wherein the drain is arranged at one of the set of multiple portions.

6. The system of claim 1, wherein the deformable bag is a leukophoresis bag.

7. The system of claim 6, wherein the leukophoresis bag is configured to be used in closed-system operation, thereby conferring sterility of the set of target materials.

8. The system of claim 1, wherein the first density is between 0.4 and 0.8 grams-per-centimeter-cubed.

9. A method for facilitating the separation of a set of target materials from a sample, the method comprising:
at a container comprising a deformable bag:
receiving a set of buoyant spheres, the set of buoyant spheres associated with a first density;
receiving the sample associated with a second density, the second density greater than the first density, wherein the sample comprises:
the set of target materials, wherein the set of buoyant spheres is configured to bind with at least a portion of the set of target materials, thereby producing a set of target-bound materials;
a set of non-target materials;
enabling an accumulation of the set of target-bound materials at a predetermined region of an internal volume of the deformable bag, thereby facilitating the separation, wherein the deformable bag is configured to be separable into a set of multiple portions, wherein the set of multiple portions comprises the predetermined region.

10. The method of claim 9, wherein the predetermined region is a superiorly-located portion of the set of multiple portions.

11. The method of claim 9, wherein the deformable bag further comprises a sealing mechanism configured to permanently separate the deformable bag into the set of multiple portions after the separation.

12. The method of claim 9, wherein the deformable bag further comprises a draining component, wherein the draining component is configured to enable a draining process of non-target materials from the deformable bag.

13. The method of claim 12, wherein the draining process is configured to be implemented after separation of the deformable bag into the set of multiple portions.

14. The method of claim 13, wherein the drain is arranged at an inferior portion of the set of multiple portions.

15. The method of claim 9, wherein the deformable bag is a leukophoresis bag.

16. The method of claim 15, wherein the leukophoresis bag is configured to be used in closed-system operation, thereby conferring sterility of the set of target materials.

17. The method of claim 9, wherein the first density is between 0.4 and 0.8 grams-per-centimeter-cubed.

* * * * *